(12) United States Patent
Amisar et al.

(10) Patent No.: US 8,613,728 B2
(45) Date of Patent: Dec. 24, 2013

(54) REMOVABLE ADAPTER FOR A SPLITTABLE INTRODUCER AND METHOD OF USE THEREOF

(75) Inventors: Shai Amisar, Tel-Aviv (IL); Ronen Radomski, Haifa (IL)

(73) Assignee: Flexicath Ltd., Misgav (IL)

( * ) Notice: Subject to any disclaimer, the term of this patent is extended or adjusted under 35 U.S.C. 154(b) by 812 days.

(21) Appl. No.: 12/084,565

(22) PCT Filed: Nov. 6, 2006

(86) PCT No.: PCT/IL2006/001277
§ 371 (c)(1),
(2), (4) Date: May 2, 2009

(87) PCT Pub. No.: WO2007/052278
PCT Pub. Date: May 10, 2007

(65) Prior Publication Data
US 2009/0318867 A1 Dec. 24, 2009

Related U.S. Application Data

(60) Provisional application No. 60/733,759, filed on Nov. 7, 2005, provisional application No. 60/789,880, filed on Apr. 7, 2006.

(51) Int. Cl.
*A61M 5/32* (2006.01)
(52) U.S. Cl.
USPC .............. 604/174; 604/178; 604/179
(58) Field of Classification Search
USPC ................................. 604/174–180
See application file for complete search history.

(56) References Cited

U.S. PATENT DOCUMENTS

| | | | |
|---|---|---|---|
| 2,937,643 A | 5/1960 | Elliot | |
| 3,185,151 A | 5/1965 | Czorny | |
| 3,547,119 A | 12/1970 | Hall et al. | |
| 3,782,383 A | 1/1974 | Thompsen et al. | |
| 4,191,186 A | 3/1980 | Keeler | |
| 4,250,880 A | 2/1981 | Gordon | |
| 4,411,654 A | 10/1983 | Boarini et al. | |
| 4,412,832 A | 11/1983 | Kling et al. | |
| 4,473,067 A | 9/1984 | Schiff | |
| 4,689,047 A | 8/1987 | Bauer | |

(Continued)

FOREIGN PATENT DOCUMENTS

| | | |
|---|---|---|
| DE | 10 2004 011217 | 10/2005 |
| EP | 0228826 | 7/1987 |

(Continued)

*Primary Examiner* — Nicholas Lucchesi
*Assistant Examiner* — Rebecca E Eisenberg
(74) *Attorney, Agent, or Firm* — Nixon & Vanderhye P.C.

(57) ABSTRACT

A securing device for preventing the splitting of a splittable sheath in the body of a treated subject, for facilitating the insertion of a splittable introducer and the splitting of said splittable sheath during removal of said introducer from the body of the subject, and optionally for interfacing said splittable introducer with other devices, comprising a "U"-like shaped portion having a distal arm and one or two proximal arms connected by a base, wherein said distal arm comprises an aperture accessible via a vertical slit passing from its upper side and terminating in said aperture, and wherein the gap defined between said distal arm and proximal arms is suitable for fitting a splittable introducer therebetween such that its splittable sheath is retained in the aperture provided in the distal arm.

34 Claims, 21 Drawing Sheets

(56) References Cited

U.S. PATENT DOCUMENTS

| | | | |
|---|---|---|---|
| 4,997,421 A | 3/1991 | Palsrok et al. | |
| 5,064,414 A | 11/1991 | Revane | |
| 5,114,256 A | 5/1992 | Lin | |
| 5,125,911 A * | 6/1992 | Grabenkort et al. | 604/250 |
| 5,141,497 A | 8/1992 | Erskine | |
| 5,250,033 A | 10/1993 | Evans et al. | |
| 5,737,803 A | 4/1998 | Tisdale | |
| 5,755,693 A | 5/1998 | Walker et al. | |
| 5,788,675 A | 8/1998 | Mayer | |
| 6,001,080 A | 12/1999 | Kuracina et al. | |
| 6,558,354 B1 | 5/2003 | Howell | |
| 6,585,703 B1 | 7/2003 | Kassel et al. | |
| 6,866,650 B2 | 3/2005 | Stevens et al. | |
| 2001/0044591 A1 | 11/2001 | Stevens et al. | |
| 2004/0167561 A1 | 8/2004 | Boucher et al. | |
| 2005/0038453 A1 | 2/2005 | Raulerson | |
| 2007/0299460 A9 | 12/2007 | Boucher et al. | |
| 2009/0143744 A1 * | 6/2009 | Bierman et al. | 604/180 |

FOREIGN PATENT DOCUMENTS

| | | |
|---|---|---|
| EP | 1293228 | 3/2003 |
| JP | 198479178 | 11/1985 |
| WO | WO 88/04185 | 6/1988 |
| WO | WO 02/94365 | 11/2002 |
| WO | WO 03/084428 | 10/2003 |
| WO | WO 2005/072807 | 8/2005 |
| WO | WO 2006/085331 | 8/2006 |
| WO | WO 2007/044510 | 4/2007 |
| WO | 2007/052278 | 5/2007 |
| WO | 166863 | 11/2010 |

* cited by examiner

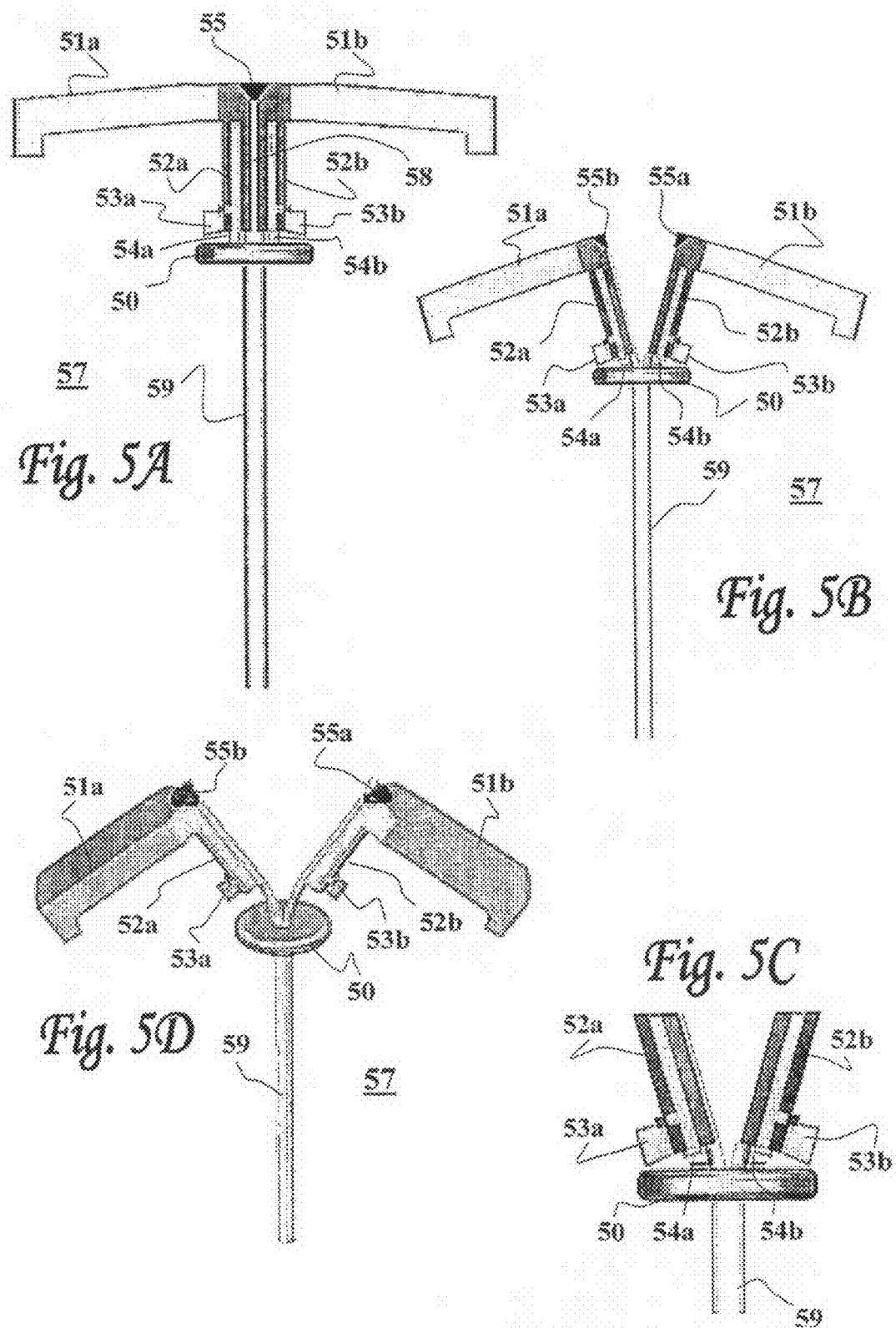

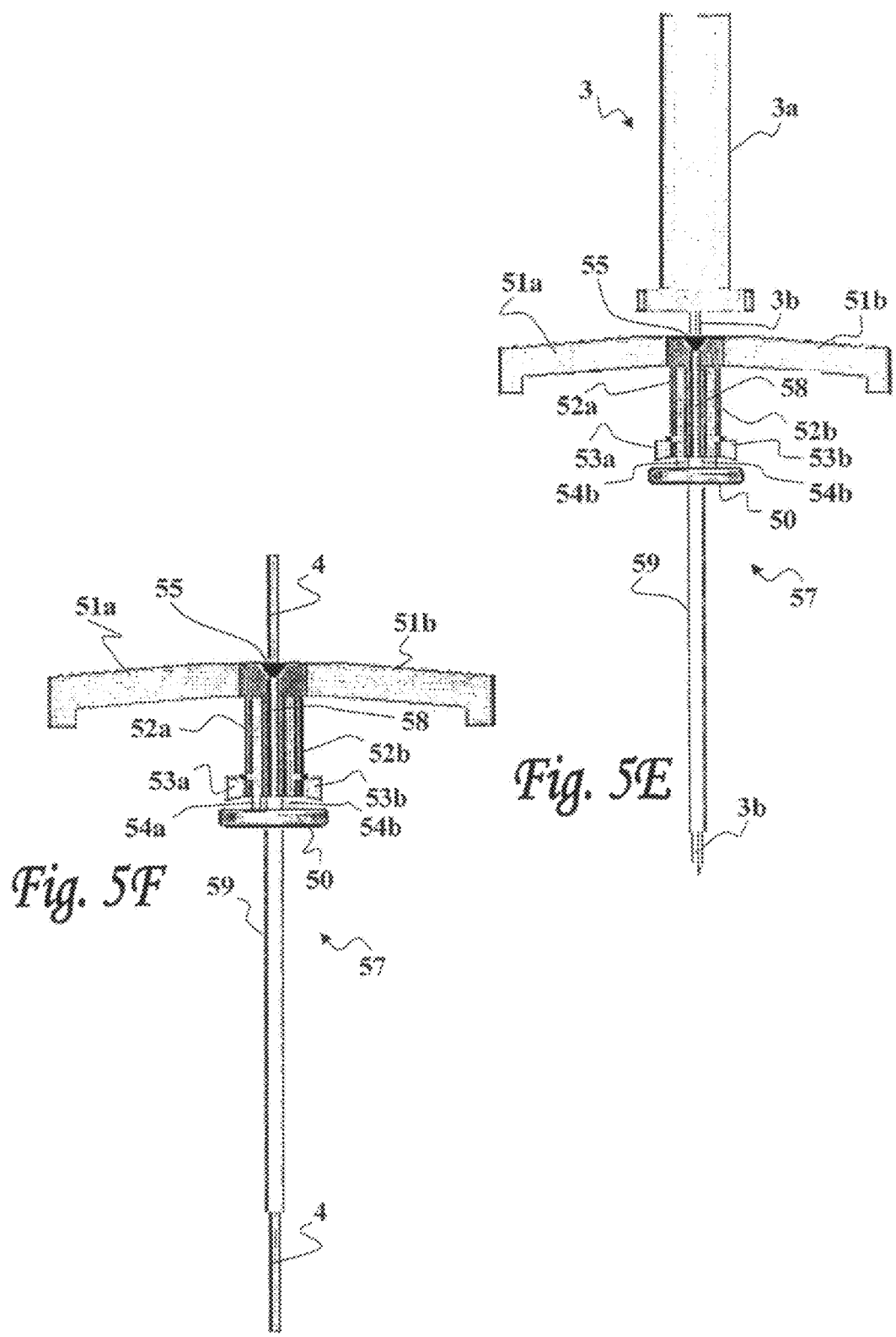

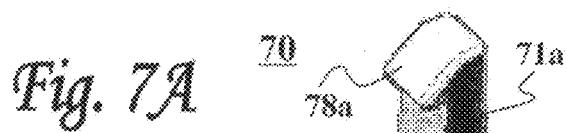
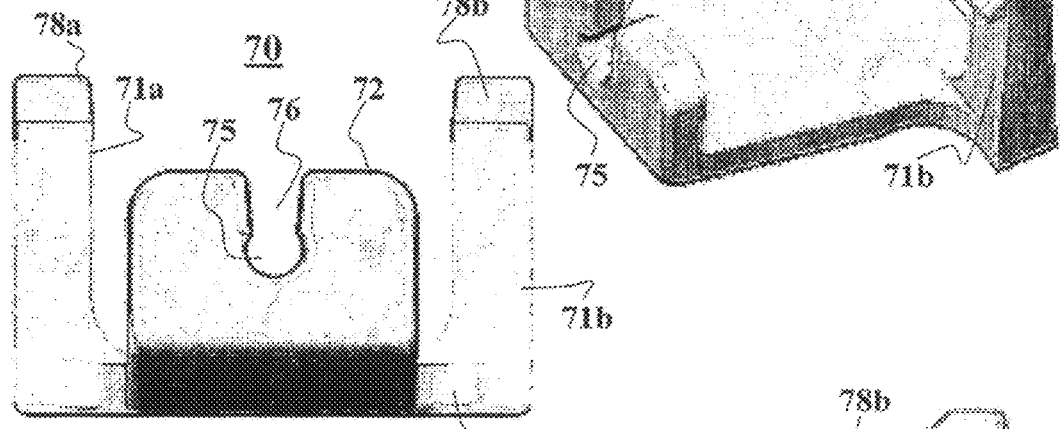
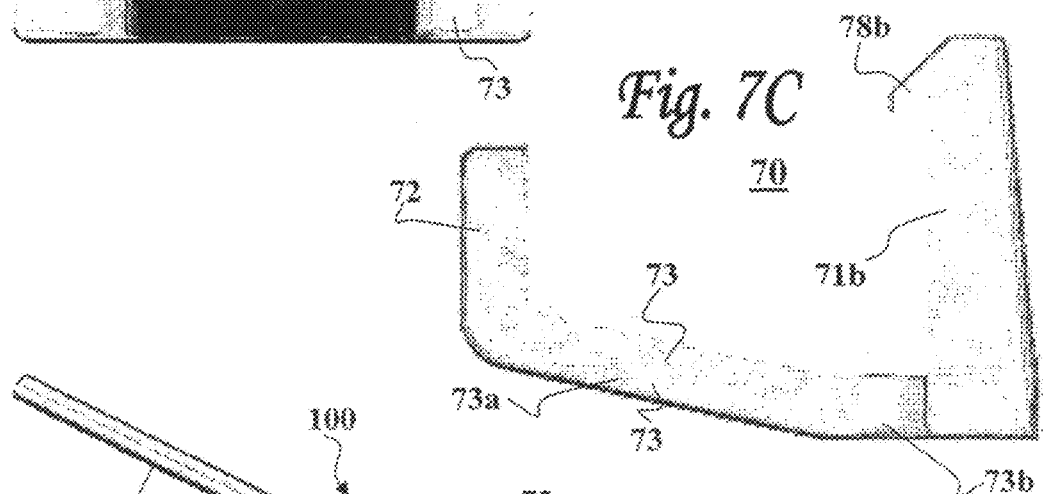
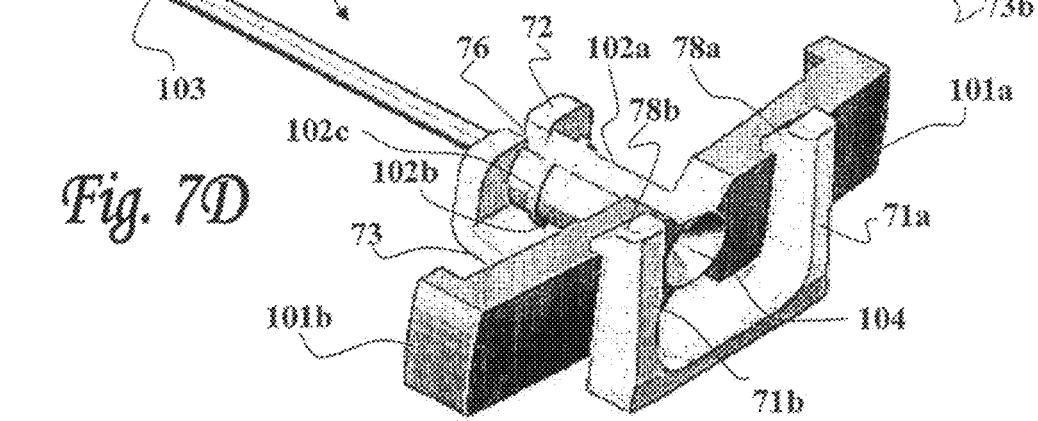

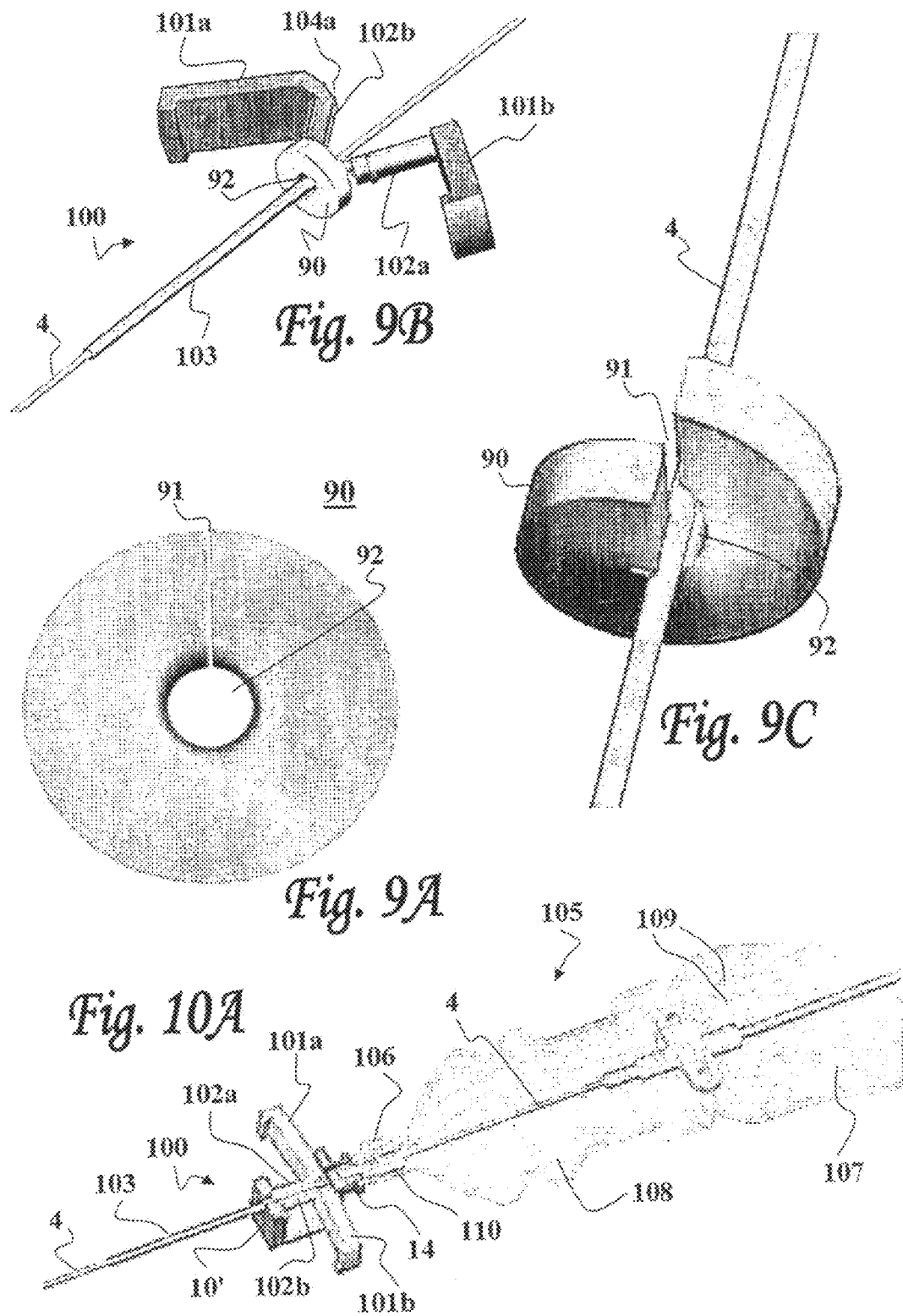

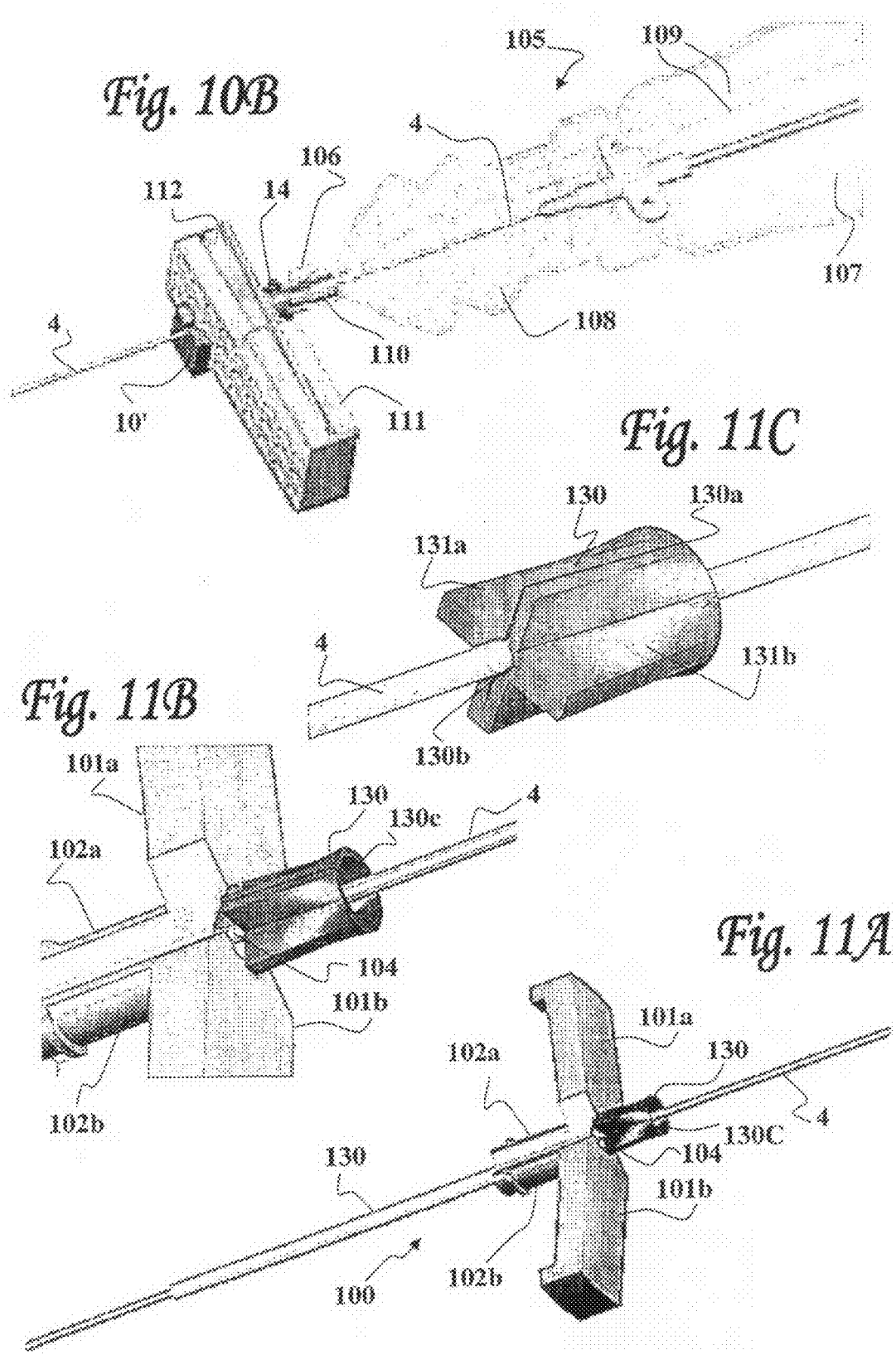

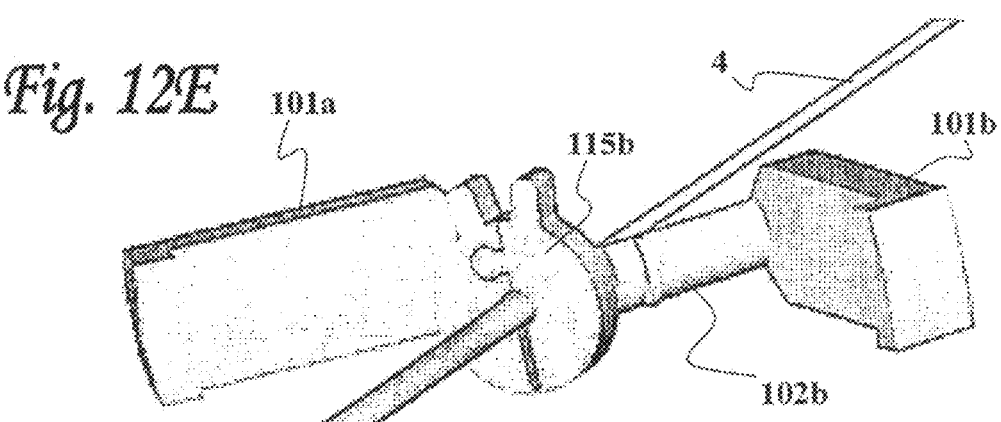
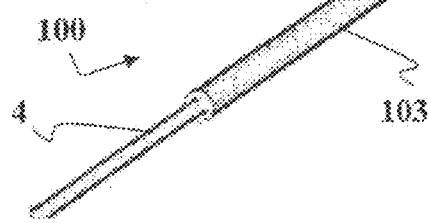
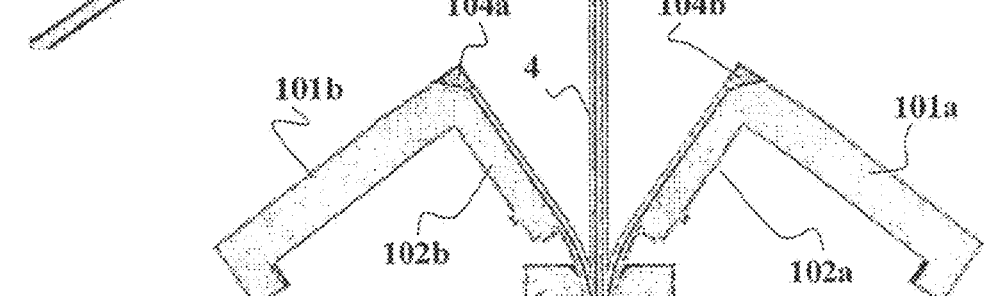

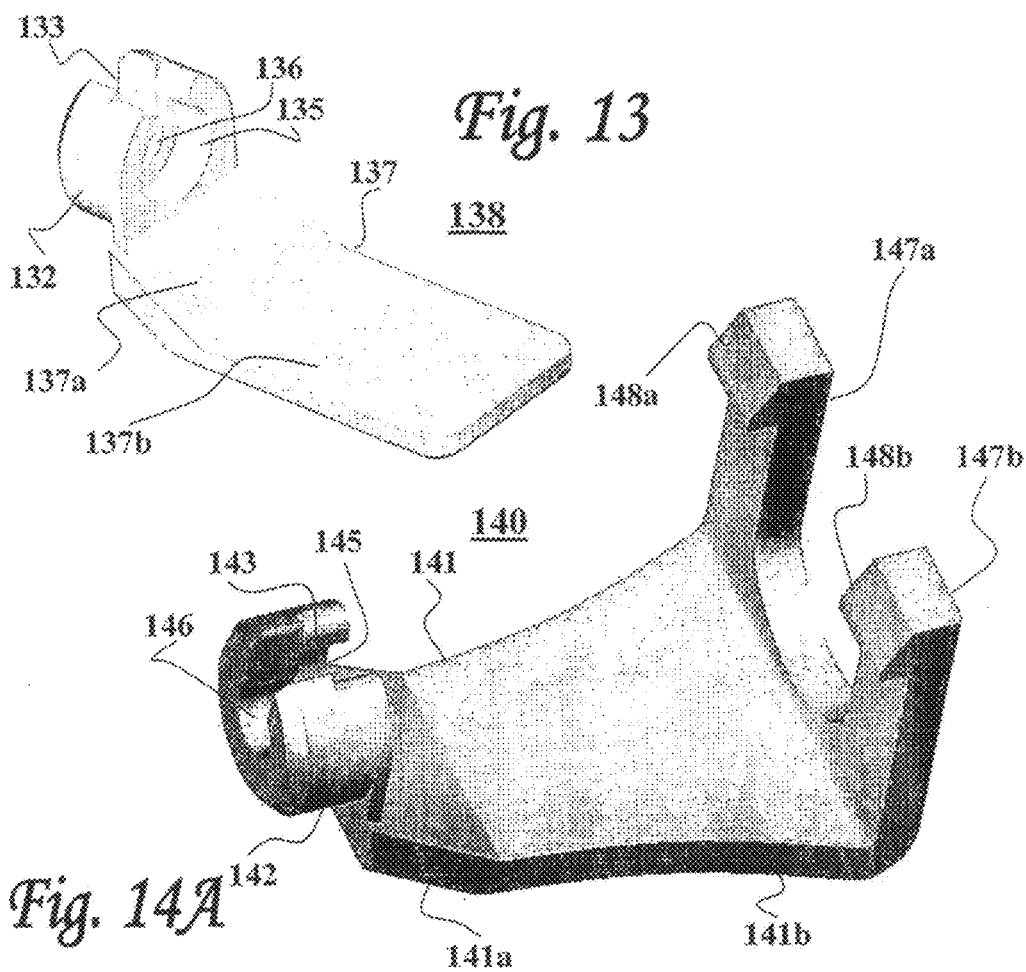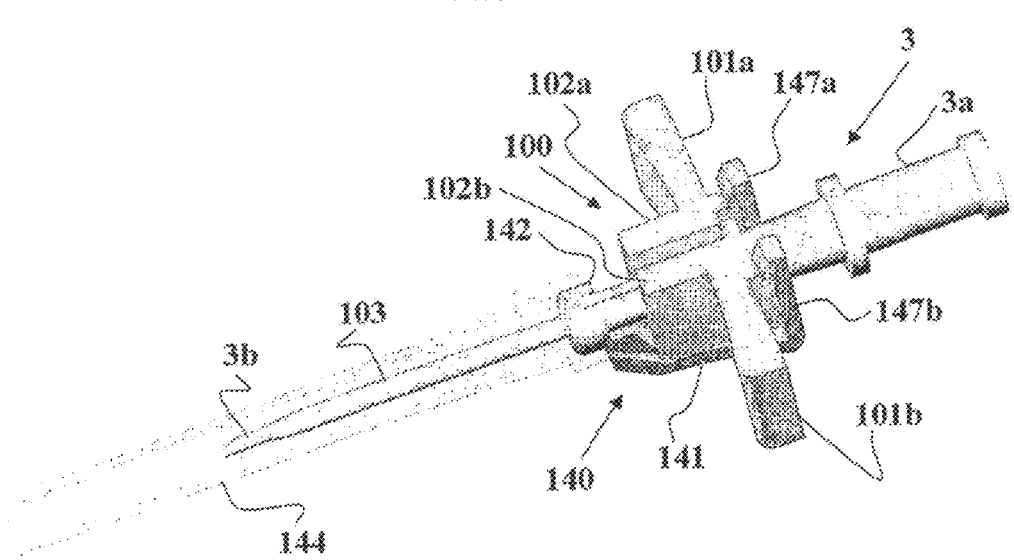

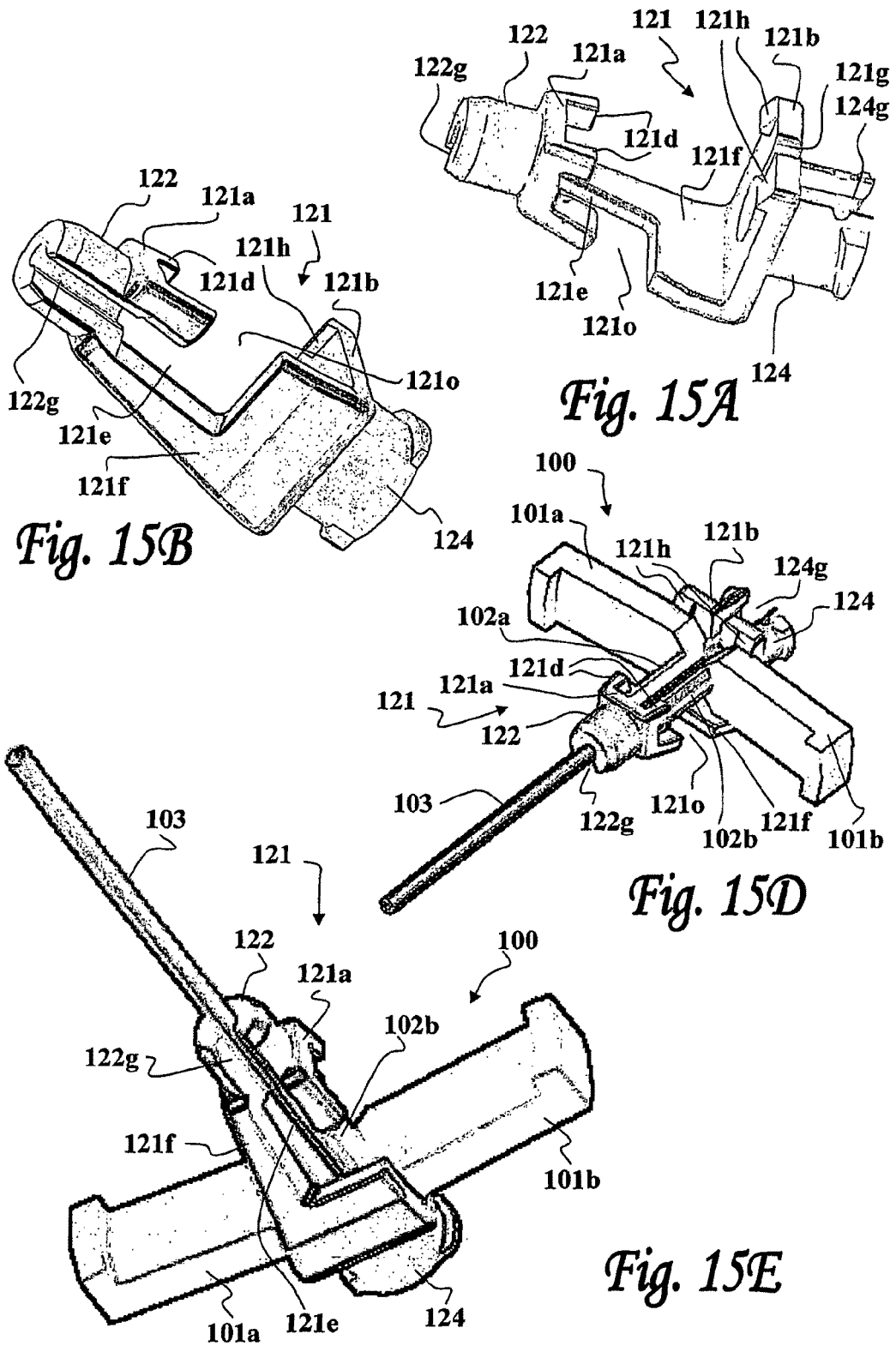

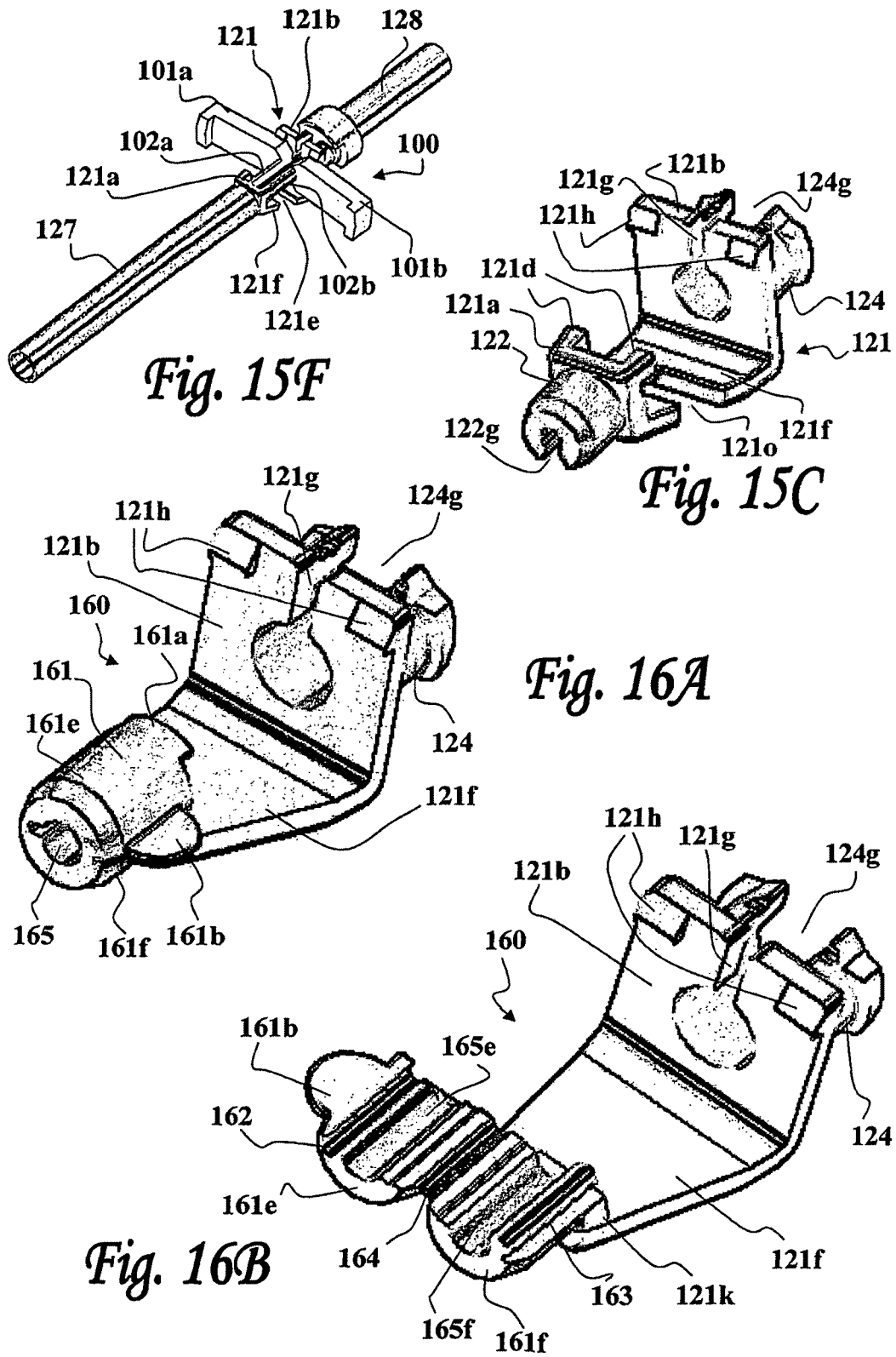

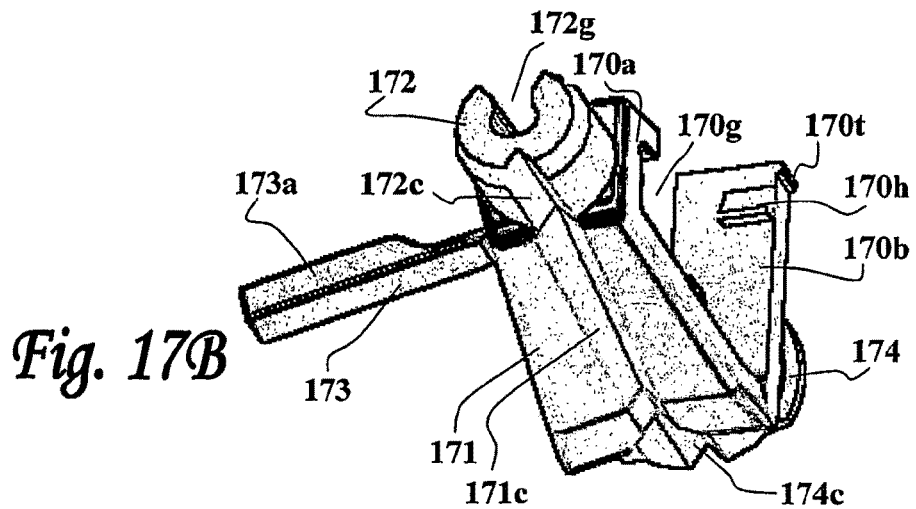
Fig. 17B
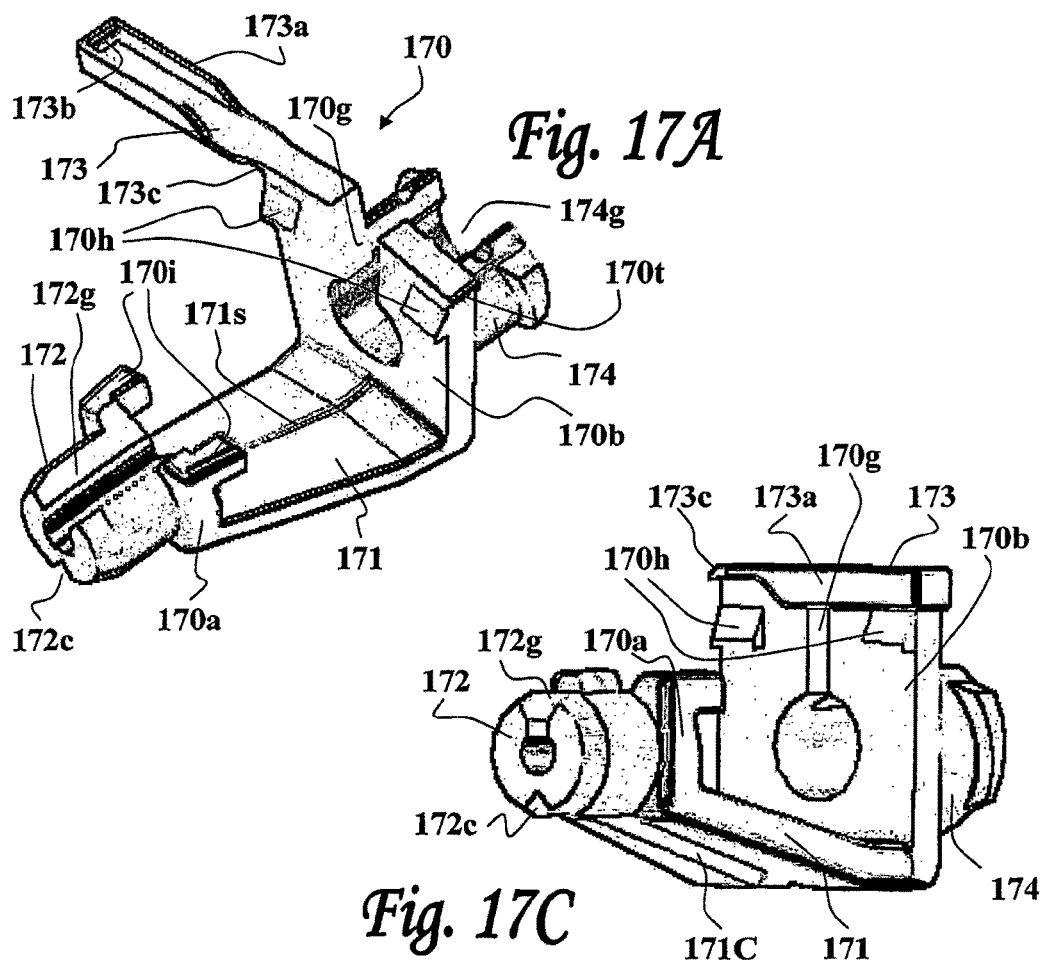
Fig. 17A
Fig. 17C

REMOVABLE ADAPTER FOR A SPLITTABLE INTRODUCER AND METHOD OF USE THEREOF

This application is the U.S. national phase of International Application No. PCT/IL2006/001277, filed 6 Nov. 2006, which designated the U.S. and claims priority to U.S. Provisional Patent Application Nos. 60/733,759, filed 7 Nov. 2005, and 60/789,880, filed 7 Apr. 2006, the entire contents of each of which are hereby incorporated by reference.

FIELD OF THE INVENTION

The present invention relates to methods and devices for inserting a catheter device. More particularly, the invention relates to methods and means for interfacing splittable introducers, securing the splittable sheath of said introducers, and for facilitating splitting thereof.

BACKGROUND OF THE INVENTION

Intravenous catheterization is typically used when frequent or continuous injections of medications or fluids for nutritional support are provided to a patient. When a long treatment period is required (e.g., longer then 3 days) a long (10 cm or longer) and soft catheter is usually used, which allows maintaining it in the patient's vein up to several months. In this procedure a single puncture of a blood vessel is made for inserting and advancing the catheter towards a selected location in a vessel wherein it is left for periodic use. In this way repetitive piercing of patient's vessels is avoided. Intravenous catheter insertion apparatuses are designed to allow inserting the catheter while preserving a sterile environment and preventing the passage of blood out via the catheter insertion apparatus.

The insertion of many intravenous catheters is carried out by placing an introducer catheter comprising an introducer needle for making the puncture (over-the-needle). After the introducer catheter is placed in the target vessel the introducer needle is withdrawn therefrom and the catheter tube may be then inserted therethrough into the selected vascular location.

Splittable catheter introducers, such as the Peel-Away® introducer, typically consist of a splittable needle-sheath having two opposing splitting tabs attached to its proximal end (i.e., trailing end) via respective shanks. The insertion of such splittable introducers into the vessel is accomplished in much the same way as the over-the-needle procedure i.e., first the blood vessel is punctured by the introducer needle contained within the needle sheath and thereafter the introducer unit is advanced into the vessel, the introducer needle is then removed, and the catheter tube is inserted into the selected vascular location. After the catheter tube is placed in the vessel the needle-sheath is removed, by retracting it from the patient's vessel and peeling it off the catheter by grasping the splitting tabs and pulling them outwardly in opposite directions, thereby tearing the sheath apart along its longitudinal length.

An intravenous catheter assembly comprising a sterile catheter insertion apparatus comprised of an integral sterile sheath containing the catheter tube therein is described in WO 03/084428. Various catheter insertion apparatuses are also described in co-pending Israeli patent application No. 166863 filed on Feb. 14, 2005, the disclosure of which is incorporated herein by reference, wherein the catheter tube contained in a sterile sleeve is inserted into the patient's vessel by utilizing catheter advancing means. However, the above mentioned catheter insertion apparatuses are designed for insertion via the conventional over-the-needle technique wherein the catheter introducer remains in the punctured vessel during the entire procedure.

JP 198479178 (Okada Yousuke) describes insertion of a catheter via a peelable sheath introduced through the nose of a patient into the stomach. A "U"-like shaped fixing device is used for retaining the catheter by a central aperture that is accessed via a slit provided in one arm, while the sheath is peeled and withdrawn outwardly via a central aperture provided in the other arm of the fixing device. The aperture of said other arm may be accessed via a slit provided therein, said aperture serves for preventing peeling of the distal section of the sheath.

EP 0,228,826 (Okada Yosuke) describes a catheter fixing device comprising an aperture, a bridge having a large hole through which the catheter may be advanced, a small hole suitable for gripping the catheter, and a slot connecting the aperture and holes through which the catheter may be moved to one of the holes. A splittable catheter sheath passes through the aperture and its proximal end is split to emerge through opposite portals of the bridge.

U.S. Pat. No. 6,558,354 (Howell Glade H.) describes an adapter that allows a needle introducer assembly having a male luer portion at its distal end to be used with a (peelable) catheter introducer that does not include a corresponding female luer portion.

U.S. Pat. No. 5,250,033 (Evans Michael A. et al) describes a peel-away introducer sheath having a pair of handle tabs and a sealing valve (or other transitional element such as a connector) detachably secured to its proximal end via a detachable threaded connector. After insertion of the catheter the introducer is withdrawn and pulled apart by pulling the tabs leaving the sealing valve over the catheter.

U.S. Pat. No. 6,585,703 (Kassel Michael) describes an introducer catheter including a tube and a proximal connector (male luer) that can be divided into two halves. The connector is used for connecting a needle guard assembly to the introducer. After insertion of the introducer the needle is retracted into the needle guard which is then removed to allow insertion of the catheter via the inserter.

In U.S. Pat. No. 4,412,832 (Kling John E. et al.) an introducer catheter assembly is described which includes a catheter tube scored along its length. The proximal end of the catheter tube is split into proximal splitting tabs located behind the location of a slidable sleeve which is telescopically mounted on the catheter tube. The slidable sleeve serves to reinforce the catheter tube and prevent split of the distal section of the catheter. After positioning an infusion catheter via the introducer lumen, the proximal end of the catheter tube can be peeled apart by pulling the proximal tabs. The introducer catheter tube is split apart as the slidable sleeve is moved toward the distal end of the introducer catheter tube until the entire catheter tube is removed.

U.S. Pat. No. 4,411,654 (Boarini Edward J.) describes an introducer catheter assembly comprising an introducer catheter tube having rupture lines along its length, and a slidable suture sleeve telescopically disposed over the introducer catheter tube. The introducer catheter is secured to a needle at a hub section by a ring. Slidable suture sleeve is originally positioned near the proximal end of catheter tube where the tube splits, such that it prevents split of distal catheter sections. After insertion of an infusion catheter the proximal splits of the tube catheter are grasped and pulled apart, thereby withdrawing the catheter tube from the patient's body and rupturing the tube along the rupture lines and eventually removing it.

The methods described above have not yet provided satisfactory solutions for interfacing between catheter appliances and splittable introducers, securing said splittable introducers, and allowing splitting their needle sheath while they are present in the body of the treated subject.

It is therefore an object of the present invention to provide means and methods for inserting a catheter tube into a selected location utilizing a splittable introducer and maintaining a sterile environment.

It is a further object of the present invention to provide means for securing and/or interfacing a splittable introducer or dilator.

It is another object of the present invention to provide an adapter for a splittable introducer capable of providing a sealed connection with auxiliary appliances such as catheter insertion apparatuses, and for facilitating the retraction and peeling of the needle sheath.

It is yet another object of the present invention to provide securing devices for preventing separation of the splittable introducer or dilator in the blood vessel, and for increasing the safety of the procedure.

An additional object of the present invention is to provide an adapter for a splittable introducer that facilitates the insertion of the catheter into the introducer.

It is still a further object of the present invention to provide an adapter for a splittable introducer and a method of using the same, which substantially minimizes movements of the catheter device in and out of the body of the treated subject during removal of the splittable introducer.

Other objects and advantages of the invention will become apparent as the description proceeds.

SUMMARY OF THE INVENTION

The present invention is directed to a securing device for preventing the splitting of a splittable sheath in the body of a treated subject, for facilitating the insertion of a splittable introducer and the splitting of said splittable sheath during removal of said introducer from the body of the subject, and optionally for interfacing said splittable introducer with other devices. Advantageously, the device of the invention allows the splitting of said splittable sheath while it is in the body of the treated subject. The present invention is also directed to methods for inserting an introducer into the body of a treated subject and for controlling the splitting of a splittable introducer in a secure manner.

In one aspect the device of the present invention comprises a removable adapter configured to receive and hold a splittable introducer and which can be utilized for securing the splittable sheath of said splittable introducer, for interfacing it with auxiliary appliances, and for facilitating the splitting of said splittable sheath.

The removable adapter may comprise a "U"-like shaped portion having a distal arm and one or two proximal arms connected by a base, wherein said distal arm comprises an aperture accessible via a vertical slit passing from its upper side and terminating in said aperture, and wherein the gap defined between said distal arm and proximal arms is suitable for fitting a splittable introducer therebetween such that its splittable sheath is retained in the aperture provided in the distal arm.

The removable adapter may comprise a single proximal arm comprising an aperture accessible via a vertical slit passing from its upper side and terminating in said aperture, wherein the proximal opening of a splittable adapter fitted into said removable adapter may be accessed via the aperture provided in the proximal arm.

The proximal face of the proximal arm may comprise connection means suitable for connecting auxiliary appliances thereto and provide a sealed passage therethrough to the aperture provided in the proximal arm. The connector means preferably comprise a longitudinal slit communicating, and preferably aligned, with the slit provided in the proximal arm. The connector means may be a type of quick connector, such as Luer lock. The connection means may comprise blades attached, or formed, on the inner rim of its longitudinal slit for facilitating the tearing of a flexible sleeve of a catheter insertion apparatus inserted thereinto.

The slits provided in the arms and in the optional connector of the removable adapter are conveniently designed to allow removal of a catheter therethrough.

An attachment surface may be attached to the proximal face of the proximal arm for preventing discomfort of the treated subject when attaching the removable adapter to its body. The attachment surface is preferably aligned with the base of the removable adapter.

The base of the removable adapter may comprise an angled portion the distal end of which is connected to the distal arm and which is elevated relative to the base portion connected to the proximal arm, wherein said angled portion may be conveniently utilized for facilitating the insertion of the splittable sheath into the body of the treated subject.

The proximal face of the distal arm of the removable adapter may further comprise a recess adapted to retain the distal tips of shanks of the splittable introducer fitted into said removable adapter.

The proximal arm of the removable adapter may optionally comprise clasps for retaining the tearing tabs of the disposable introducer fitted thereinto.

In yet another preferred embodiment of the invention the distal arm comprises a vertical slit which pass from its bottom side and terminates in the aperture provided therein, wherein said vertical slit connects to a slit passing along a longitudinal portion of the base of the securing device, and wherein said slit passing along the longitudinal portion of the base may be accessed via a lateral opening provided in said base.

The securing device may comprise enclosing means attached to the distal arm, wherein said enclosing means comprises a base section, attached to said distal arm, and a fastening section connected to said base section by means of a hinge, where said enclosing means may further comprise a locking mechanism.

The securing device may comprise locking means attached to the proximal arm. Said locking means may comprise a locking arm attached to an upper side corner of said proximal arm by means of hinge.

The base of the securing device may comprise a twisting channel passing along the length of the bottom side thereof and allowing bending said base.

Additionally or alternatively, the proximal arm is connected to the base of the securing device by means of a hinge such that it may be turned about said hinge.

Additionally or alternatively, the distal arm may further comprise fastening means adapted to hold the distal portion of the shanks of a splittable introducer.

In another aspect the device of the present invention comprises a securing device adapted to hold the splittable sheath of a splittable introducer and facilitate splitting thereof in a controlled and secure manner. The securing device is preferably designed to be attached to the distal end of the shanks of the splittable introducer.

According to another preferred embodiment of the invention the securing device comprises an aperture adapted to receive and hold the splittable sheath of the splittable introducer, and wherein said aperture communicated with a hollow passage and/or a slit passing between said aperture and the edge of the securing device.

A proximal face of the securing device may be attached to the distal tips of the shanks of splittable introducer. Additionally or alternatively, the securing device may be an integral part of the splittable introducer, which is made such that a proximal face of said securing device is attached to the distal tips of the shanks of the splittable introducer.

In another embodiment of the invention the securing device may be constructed in a circular form having a central aperture and a hollow passage and a slit extending radially therefrom, and two releasing tabs provided near, and in substantially equal distances from, said hollow passage, wherein said hollow passage accesses said central aperture of said securing device and terminates near the circumference of said securing device. The slit is preferably located opposite to said hollow passage, and it may comprise a curved portion defining a locking mechanism which may be opened by pressing the releasing tabs towards each other.

The proximal face of the securing device may comprise an oval (e.g., elliptic) recess containing the aperture of said securing device and defining lateral grooves for centering the securing device and preventing rotation thereof during the splitting of the splittable sheath of the splittable introducer.

The securing device may be an integral part of a piercing needle assembly comprising a piercing needle affixed to a handle, and a breakable element connecting between said securing device and said piercing needle assembly.

According to yet another preferred embodiment of the invention the securing device comprises a securing arm and a substantially perpendicular attachment surface attached thereto, wherein said securing arm comprises an aperture adapted to receive and hold the splittable sheath of a splittable introducer, and wherein said aperture may be accessed by an opening provided between the upper side of said securing arm and an upper part of said aperture, and wherein said opening is configured to allow passage of a catheter device therethrough.

The proximal face of the securing arm may comprise a fastening recess adapted to retain the distal ends of the shanks of the splittable introducer. The inner face of the fastening recess may comprise grooves configured to receive respective flanges formed near the distal ends of the shanks.

According to a further preferred embodiment of the invention the securing device comprises two holding arms connected by a base, wherein said arms are configured to hold the distal end of the shanks of the splittable introducer and secure a portion of the splittable sheath near the tips of said shanks. An opening may be provided between said arms for conveniently removing a catheter device passing therethrough after splitting said splittable introducer.

The inner side of the base of the securing device may comprise a detent mechanism adapted to fit in a groove between the shanks of the splittable introducer and thereby prevent rotations of said securing device and enhance its grip in said shanks.

The holding arms may comprise an inner groove adapted to receive a respective flange formed (or attached) on the outer surface of a distal end portion of the shanks.

According to a further preferred embodiment of the invention, the securing device is configured to receive a needle guard attachment.

According to a further preferred embodiment of the invention, the securing device is configured to facilitate easy insertion of the catheter into the introducer by providing a relatively wide entry port leading to the opening of the splittable sheath of the introducer via concentric and centering tapering passage. The base (or attachment surface) of the securing device is preferably adapted to prevent rotations thereof about the catheter tube passing therethrough during insertion thereof. In addition, the base (or attachment surface) of the securing device may comprise a self-adhering strip attached thereto, wherein said self-adhering strip is covered by a removable cover, which may be removed by user after completing insertion of the splittable introducer into the body of the treated subject, for attaching the removable adapter therewith to the body of said subject.

The present invention is also directed to a method for inserting a splittable introducer into the body of a treated subject, for inserting a catheter device through said splittable introducer, and for splitting said introducer in a controlled and secured manner, wherein said method comprises: providing a device of the invention and fitting a splittable introducer thereinto; inserting a piercing needle into said splittable introducer and inserting the splittable sheath of said introducer into the body of the treated subject; removing said piercing needle and inserting a catheter device through said introducer; splitting said introducer by laterally pulling the tearing tabs of said introducer, thereby gradually retracting portions of the splittable sheath via the aperture of said removable adapter or securing device and concurrently splitting them until the entire sheath is retracted and split, removing said removable adapter or securing device by removing the catheter device passing through its aperture via the slit or opening of, or by splitting, said removable adapter or securing device. In this way the introducer is split after completing the insertion of the catheter, without the need to pull it back first, such that the only operation required is pulling the splitting tabs sideways.

The present invention is also directed to a method for extracting a splittable sheath from the body of a treated subject without the need to pull out portions of the catheter passing therein.

BRIEF DESCRIPTION OF THE DRAWINGS

The present invention is illustrated by way of example in the accompanying drawings, in which similar references consistently indicate similar elements and in which:

FIG. 5A is a side view of a splittable introducer of the invention having an integral securing ring;

FIGS. 5B to 5D demonstrates splitting the introducer having an integral securing ring shown in FIG. 5A;

FIG. 5E demonstrates the splittable introducer shown in FIG. 5A with a piercing needle;

FIG. 5F demonstrates the splittable introducer shown in FIG. 5A with a catheter device;

FIG. 7A is a perspective view of a removable adapter of the invention which comprises lateral fasteners;

FIGS. 7B and 7C are front and side views, respectively, of the removable adapter shown in FIG. 7A;

FIG. 7D demonstrates assembling a splittable introducer into the removable adapter shown in FIGS. 7A to 7C;

FIG. 9A is a front view of a removable securing ring of the invention for a splittable introducer;

FIG. 9B demonstrates splitting a splittable introducer secured by the removable securing ring shown in FIG. 9A;

FIG. 9C demonstrates removing the removable securing ring shown in FIG. 9A;

FIGS. 10A and 10B demonstrates a removable adapter of the invention that is suitable to be used with a catheter cutter device and with a splittable introducer;

FIGS. 11A to 11C show a removable slender passage suitable for use with the devices of the invention;

FIGS. 12E, 12F, and 12G, are front perspective, rear perspective, and side, views, respectively, demonstrating splitting a splittable introducer secured by the removable securing device shown in FIGS. 12C and 12D;

FIG. 12H demonstrates the removable securing device and a catheter device passing therethrough after removal of the splittable introducer;

FIG. 13 is a perspective view of a removable securing device of the invention that is configured to receive a needle guard;

FIG. 14A is a perspective view of a removable adapter of the invention that is configured to receive a needle guard;

FIG. 14B is a perspective view of the removable adapter shown in FIG. 14A with a splittable introducer including a piercing needle and a needle guard covering the needle;

FIGS. 15A to 15F illustrate an embodiment of the removable adapter of the invention having a slit along a distal section of its bottom side;

FIGS. 16A to 16E illustrate an embodiment of the removable adapter comprising enclosing means;

FIGS. 17A to 17H illustrate an embodiment of the removable adapter comprising locking means.

DETAILED DESCRIPTION OF PREFERRED EMBODIMENTS

The present invention provide means for interfacing splittable introducers (e.g., PeelAway), securing the splittable sheath of said introducers, and/or for facilitating splitting thereof while said splittable sheath is in the body of the treated subject. These aims are primarily achieved by using a removable adapter configured to receive and hold the splittable introducer and optionally provide convenient connection means thereto, secure its splittable sheath, and allow the operator to split it while it is in the body of the treated subject. A number of embodiments of the invention which will be now described in details can be used to achieve all, or part of, these aims.

Figure 1A:
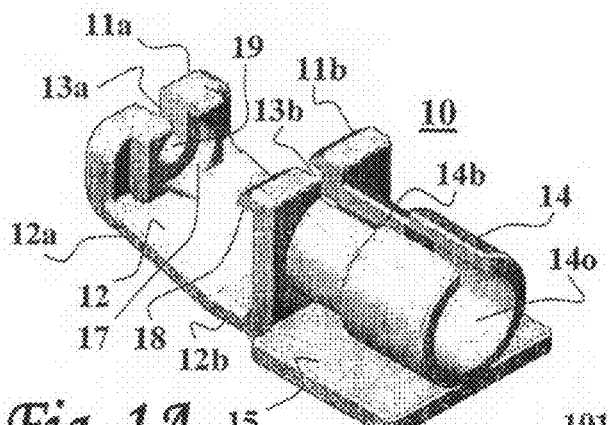
FIG. 1A is a perspective view of a removable adapter of the invention.

FIG. 1A illustrates a removable adapter 10 of the invention. Removable adapter 10 has a "U"-like shaped portion comprising a first arm 11a comprising a slit 13a passing from its upper end towards an aperture 19 provided at its center. The proximal face of first arm 11a comprises a recess 17, concentric with aperture 19. A second arm 11b of removable adapter 10 is spaced apart from the first arm 11a, where said arms are connected by the base 12 of the "U"-like shaped portion of removable adapter 10.

Second arm 11b also comprises a slit 13b passing from its upper end toward its center wherein an aperture is provided. The slits in arms 11a and 11b provides a path for releasing the catheter tube passed therethrough and removing adapter 10 after completing the insertion procedure. The central aperture of second arm 11b is adapted for accessing the inner lumen of splittable sheath 103 (FIG. 1B) therethrough. Second arm 11b further comprises a connector 14 attached to (or formed on) the proximal face of arm 11b and comprising a concentric bore adapted for communicating with a proximal opening of sheath 103 when fitted in removable adapter 10. Connector 14 further comprises a slit 14b corresponding in location and depth with slit 13b provided in second arm 11b, such that said slit provides access into the concentric bore of connector 14.

Connector 14 is preferably mounted on an attachment surface 15 which is conveniently aligned with the bottom side of the second arm 11b to prevent discomfort to the treated patient, which may be caused when attaching connector 10 to its body. A distal portion 12a of base 12 connecting the arms 11a and 11b is preferably made angled relative to a proximal portion 12b thereof that is preferably aligned with attachment surface 15, such that the side of the distal portion 12a attached to first arm 11a is elevated with respect to the side attached to the proximal portion 12b, which alleviates the steps of piercing the tissues of the treated subject (not shown) and introducing the splittable sheath 103 into its body.

Figure 1B:
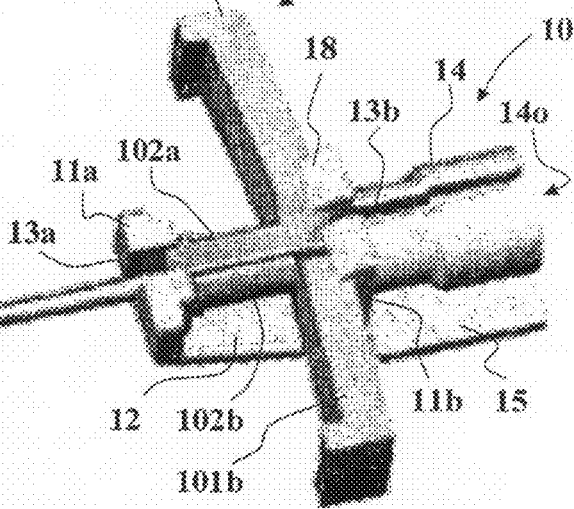
FIG. 1B demonstrates fitting a splittable introducer into the removable adapter shown in FIG. 1A.

Recess 17 provided in the inner wall of first arm 11a, which is preferably concentric with aperture 19, is adapted for holding the distal tips of shanks 102a and 102b of splittable introducer 100, as demonstrated in FIG. 1B. In this way splittable introducer 100 may be fitted into removable adapter 10 by positioning splittable sheath 103 inside aperture 19 via the inner opening of aperture 19, or via slit 13a, and advancing it therethrough until the distal tips of shanks 102a and 102b are introduced into recess 17 after which splittable introducer 100 may be snapped into the "U"-like shaped portion of adapter 100 by pushing splitting tabs 101a and 101b down towards base 12 until their upper faces are clasped by snaps 18 provided on the upper part of the distal face of second arm 11b.

Figure 1C:
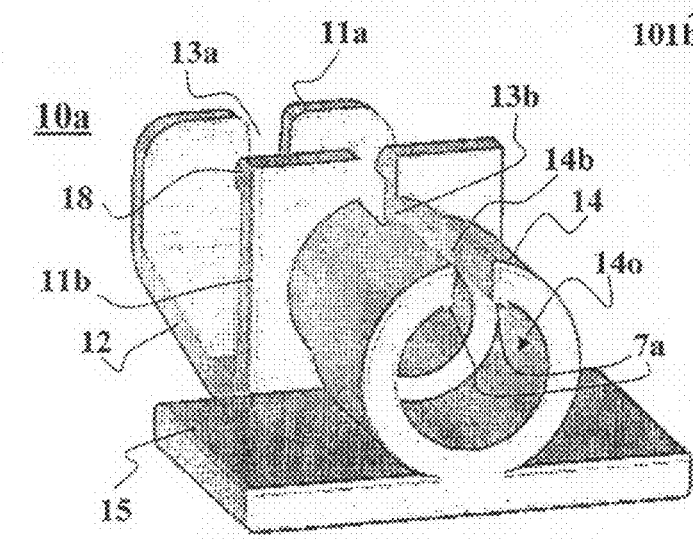
FIG. 1C is a perspective view of a removable adapter, as shown in FIG. 1A, comprising tearing blades.
Figure 1D:
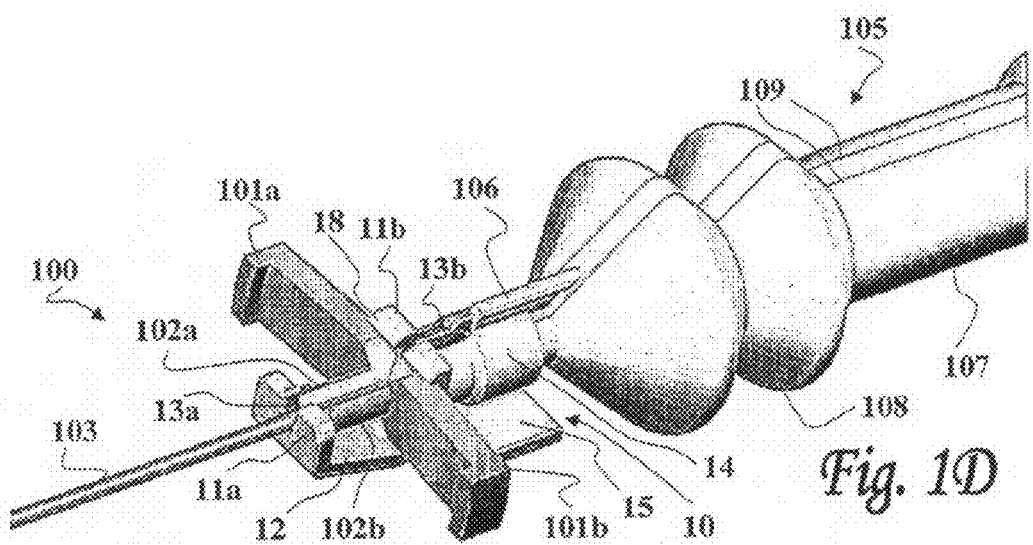
FIG. 1D demonstrates connecting a catheter insertion apparatus to the removable adapter of the invention.

FIG. 1D demonstrates attaching catheter insertion apparatus 105 to the removable adapter 10 of the invention. This connection may be achieved by inserting the tapering hollow tip of sleeve 107 of insertion apparatus 105 into connector 14 via its opening 14o such that a tearing tab 106 formed on said tapering tip is introduced in slit 14b of adapter 10. Catheter device (not shown) provided inside flexible sleeve 107 of insertion apparatus 105 may be advanced into sheath 103 of splittable introducer 100 by grasping portions thereof via flexible sleeve 107 and pushing the same distally thereby pressing and shrinking resilient/elastic portion 108 of flexible sleeve 107 (e.g., bellow).

After completing the insertion of the catheter device the operator may tear insertion apparatus 105 by fastening removable adapter 100 in its location and pulling tearing tab 106 upwardly. The tearing of flexible tube 107 is performed along tearing lines 109 and may be facilitated by blades 7a provided on the inner edges of slit 14b in connector 14, wherein the sharp edge of said blades is directed inwardly towards the hollow interior of connector 14, as exemplified in the removable adapter 10a shown in FIG. 1C. In this way pulling tearing tab 106 upwardly results in introducing cuts into the upper portion of the end section of flexible tube 107 by blades 7a.

It should be noted that assembly of the removable adapter of the invention and the splittable introducer can be performed either during the manufacturing process or by the end-user before introducing the sheath of the splittable introducer into the body of the treated subject.

Of course, the catheter device may be also inserted into the body of the treated subject by other means, for example, by manually pushing portions of the catheter device distally via opening 14o. After inserting the catheter device the splittable introducer may be removed by fixating removable adapter 10 in place and laterally pulling tearing tabs, 101a and 101b, of splittable introducer 100, which in turn splits shanks, 102a and 102b, retracts portions of sheath 103 via aperture 19 and concurrently splits them. After pulling and splitting the entire length of splittable sheath 103 removable adapter 10 can be removed by removing catheter device passing therein via slits 13a, 13b and 14b.

The catheter insertion steps and the tearing of the flexible sheath are also described in co-owned international patent application No. PCT/IL2006/000194.

Removable adapter 10 (and 10a) may be manufactured by injection molding from a type of polymer, such as but not limited to, polypropylene. The diameter of aperture 19 is adapted to allow sheath 103 of splittable introducer 100 to be easily received therein, and the width of slit 13a is similarly configured to allow easy removal of the catheter device passing via aperture 19. For example, in a specific embodiment of the invention the diameter of aperture 19 may be generally in the range of 0.5 to 5 mm, preferably about 1.6 mm, and the width of slit 13a may be generally in the range of 0.5 to 5 mm, preferably about 1.5 mm. Similarly, the gap between arms 11a and 11b should be adapted to receive shanks 102a and 102b therebetween, for example, said gap may generally be in the range of 5 to 20 mm, preferably about 11 mm. Connector 14 is preferably a type of quick connector (e.g., Luer lock). The angle ($\theta$ shown in FIG. 2A) of distal portion 12a of base 12 relative to it proximal portion 12b and/or attachment surface 15 is generally in the range of 15° to 60°, preferably about 30°. Blades 7a may be manufactured from a rigid material, such as metal, polycarbonate, polypropylene, and they may be attached to adapter 10 by gluing, molding or manufactured as an integral part thereof. The length of blades 7a is generally in the range of 0.5 to 3 mm, preferably about 2 mm, and their thickness is preferably about 0.5 mm.

Figure 2A:
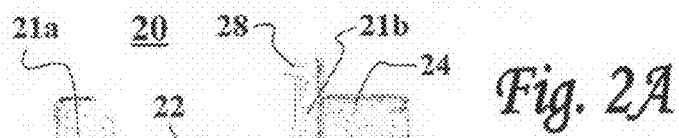
FIG. 2A is a side view of another removable adapter of the invention.

A side view of another removable adapter of the invention 20 is shown in FIG. 2A. Removable adapter 20 is designed to facilitate the splitting of splittable introducers and sealing rings or slender/tapering passage elements (e.g., 55 in FIG. 5, 130 in FIG. 11) by laterally pulling the splitting tabs of the introducer and eliminating the need to retract the splittable sheath outwardly before splitting it. Adapter 20 is substantially similar in shape and structure to adapter 10 shown in FIGS. 1A to 1D, and it comprises similar apertures and slits. As shown in FIG. 2A adapter 20 comprises a "U"-like shaped portion comprising arms 21a and 21b and base 22 connecting them, wherein a distal portion 22a of base 22 is angled ($\theta$, 15° to 60°) relative to proximal portion 22b thereof. Arm 21b comprises clasps 28 and connector 24 attached to its distal face.

Figure 2B:
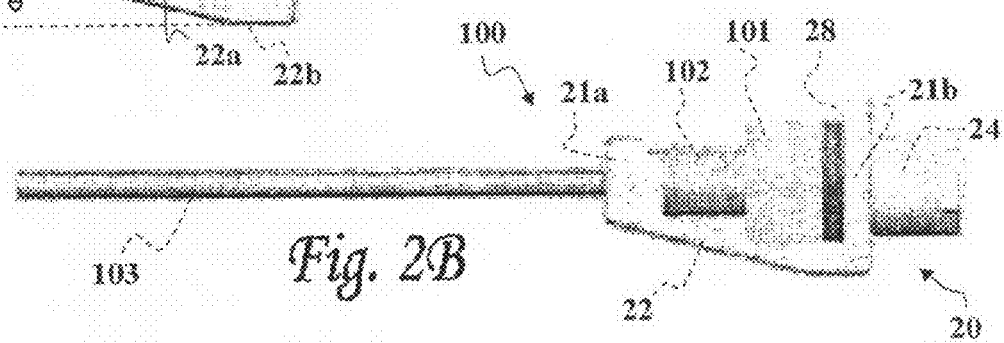
FIG. 2B demonstrates fitting a splittable introducer into the removable adapter shown in FIG. 2A.

Connector 24 of adapter 20 is preferably a type of quick connector (e.g., Luer lock) which is relatively short in length (e.g., 3-6 mm) and thus an attachment surface (15, FIGS. 1A-1D) is not required in this implementation. FIG. 2B demonstrates assembling splittable introducer 100 into removable adapter 20. The steps of inserting the catheter device into the body of the treated subject, splitting and removing the splittable introducer 100, and removing removable adapter 10, are substantially similar to the steps described with reference to FIGS. 1A to 1D.

Figure 3A:
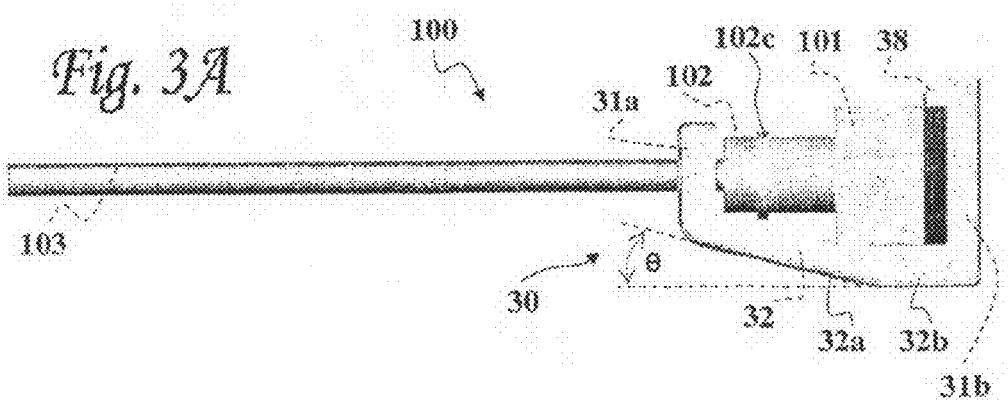
FIG. 3A is a side view of a removable adapter of the invention having a splittable introducer fitted therein, wherein the removable adapter does not comprise connector means.
Figure 3B:
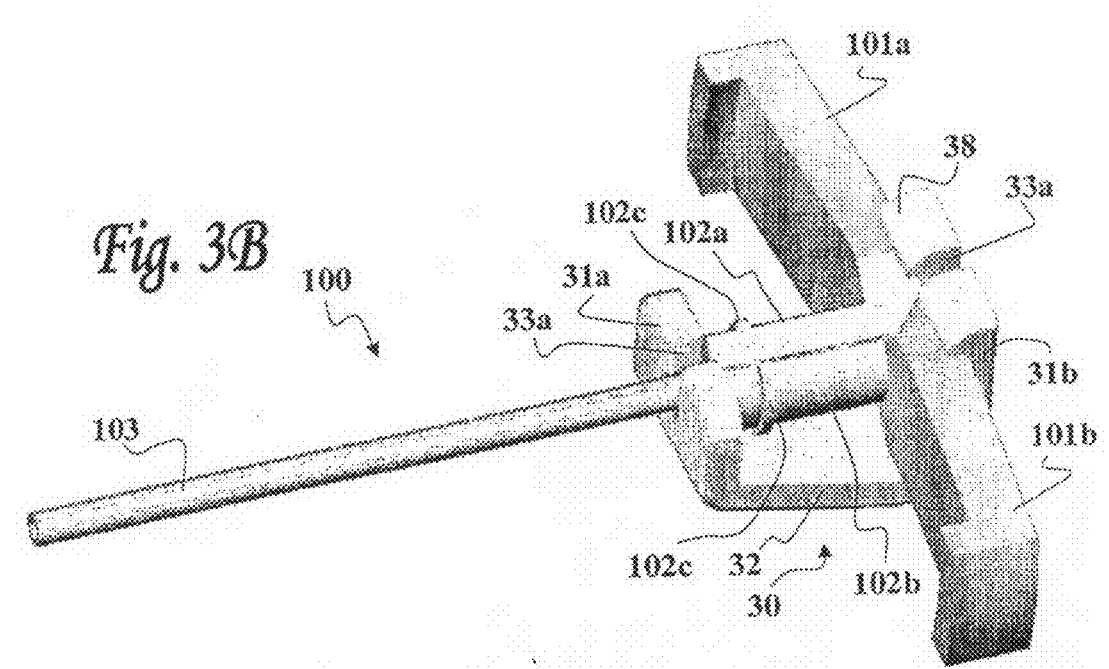
FIG. 3B is a perspective view of a splittable introducer and removable adapter assembly shown in FIG. 3A.

FIG. 3A is a side view of a removable adapter 30 of the invention having a splittable introducer 100 assembled thereto, wherein adapter 30 does not comprise connector means. Adapter 30 is substantially similar in shape and structure to adapter 10 shown in FIGS. 1A to 1D, it comprises similar apertures and slits, and the steps of inserting sheath 103 of splittable introducer 100, splitting said sheath, and removing adapter 30 thereafter, are also substantially similar. Adapter 30 comprises a "U"-like shaped portion comprising arms 31a and 31b and base 32 connecting them, wherein a distal portion 32a of base 32 is angled ($\theta$, 15° to 60°) relative to proximal portion 32b thereof. Arm 31b comprises clasps 38 and an aperture provided in it (not shown) is used to access the inner lumen of sheath 103. Removable adapter 30 substantially prevents rotations of the adapter and splittable introducer assembly when placed on the body of the treated subject due to the flat surface of base 32 which prevents rotations thereof when pressed against the body of the treated subject. Moreover, removable adapter 30 advantageously prevents accidental splitting of the splittable introducer 100. FIG. 3B is a perspective view of the splittable introducer 100 and removable adapter 30 assembly.

Figure 4A:
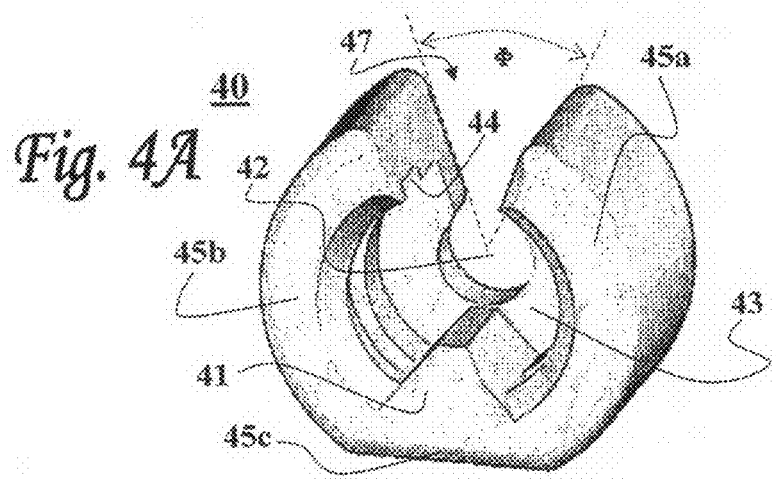
FIG. 4A is a perspective view of a removable securing device of the invention for a splittable introducer.

FIG. 4A is a perspective view of a removable securing device 40 of the invention. Removable securing device 40 is adapted to hold shanks 102a and 102b of splittable introducer 100 and facilitate splitting thereof while said splittable sheath 103 is in the body of the treated subject (not shown). Securing device 40 may be configured in horseshoe like shape having holding arms 45a and 45b, and a flat base 45c connecting said arms, and which may be used as an attachment surface for attaching to the body of the treated subject (not shown). The proximal face of removable securing device 40 may comprise a sheath gripping part 43 comprising an aperture 42 adapted for gripping splittable sheath 103 near the distal tips of shanks, 102a and 102b.

Securing device 40 may comprise a detent mechanism for enhancing the grip of introducer 100 by securing device 40 and for preventing rotation thereof when fitted in securing device 40. Detent mechanism may be implemented as a tapering portion 41 formed on the inner side of base 45c. Tapering portion 41 is adapted to fit into groove 2a (or 2b) provided between shanks 102a and 102b of splittable introducer 100 and thereby improve the grip of the introducer by enhancing the friction forces applied by removable securing device 40. Detent mechanism may further comprise an inner groove 44 formed on the distal face of holding arms 45a and 45b, wherein said inner groove 44 is adapted to receive respective flanges 102c (Shown in FIG. 3B) formed near the distal ends of shanks 102a and 102b. Inner groove 44 and respective flanges 102c allows snapping splittable introducer 100 into securing device 40 and prevents it from sliding distally over sheath 103.

Figure 4B:
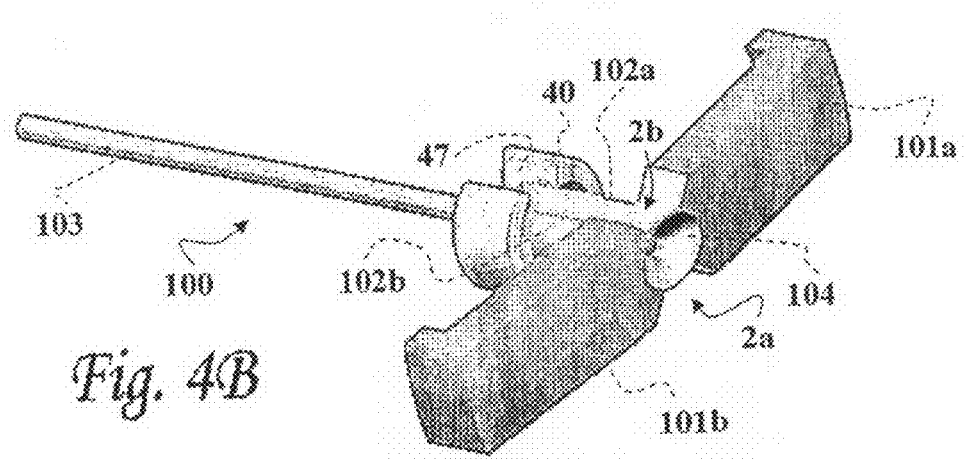
FIG. 4B demonstrates fitting a splittable introducer into the removable securing device shown in FIG. 4A.

FIG. 4B demonstrates the assembly of splittable introducer 100 into removable securing device 40. The assembled device may be conveniently used to insert splittable sheath 103 into the body of the treated body (not shown) using conventional methods (e.g., over the needle). After the step of inserting the introducer, a catheter device (not shown) may be inserted through sheath 103 via opening 104 of splittable introducer 100. As shown in FIG. 4B, opening 104 may be formed in a shape of, or comprise, a conical passage the tapering end of which is adapted to tightly fit over the outer surface of the catheter device passing therein and thereby prevent backflow of fluids (e.g., blood) therethrough. Following insertion of the catheter, splittable introducer 100 may be removed by fixating removable securing device in place and laterally (i.e., in opposite directions) pulling splitting tabs, 101a and 101b, thereby releasing the grip applied on shanks, 102a and 102b, by removable securing device 40, splitting shanks, 102a and 102b, and retracting and concurrently splitting portions of splittable sheath 103.

Of course the shape of tapering opening 104 may be other than the conical (e.g., triangular) shaped passage demonstrated hereinabove. Furthermore, a similar passage (e.g., a rubber septum/valve), namely, that allows the insertion of the catheter tube therethrough but which prevents backflow of fluids, may be provided as an integral or separate part of the various removable adapters of the present invention.

In this way removable securing device 40 may facilitate removal of splittable introducer 100 while its splittable sheath 103 is in the body of the treated subject (not shown), and said splittable introducer 100 is removed after the entire sheath 103 is split (and consequently, retracted). Thereafter, removable securing device 40 may be also removed by removing catheter device (not shown), passing through aperture 42, via opening 47 provided in the side opposite to base 45c.

Removable securing device 40 may be manufactured by injection molding from a type of polymer, such as but not limited to, polypropylene, and its geometrical dimensions should be configured in accordance with the geometrical dimensions of conventional splittable introducers, or modifications thereof. For example, the outer diameter of removable securing device 40 may generally be in the range of 6 to 20 mm, preferably about 8 mm, and its inner diameter may generally be in the range of 0.5 to 6 mm, preferably about 4 mm. The width of removable securing device 40 may generally be in the range of 15 to 60 mm, preferably about 30 mm. The diameter of aperture 42 may generally be in the range of 0.5 to 6 mm, preferably about 1.6 mm, and the angle $\Phi$ of opening 47 may generally be in the range of 15° to 60°, preferably about 30°.

FIG. 5A is a side view of a secured splittable introducer 57 of the invention having an integral securing ring 50. Splitting tabs, 51a and 51b, and splittable sheath 59, of secured splittable introducer 57 are substantially similar to those provided in conventional splittable introducers. Shanks, 52a and 52b, of secured splittable introducer 57 comprise detaching members, 53a and 53b, attached or formed perpendicular to said shanks at their distal ends. Distal tips of shanks 53a and 53b comprises detachable connectors, 54a and 54b, which attach securing ring 50 to said shanks, 52a and 52b, respectively.

Detachable connectors, 54a and 54b, connects the upper surface of ring 50 to the distal tips of shanks, 53a and 53b, respectively, and thereby prevents it from sliding over, and/or rotating about, splittable sheath 59 of secured splittable introducer 57. Thus, securing ring 50 may be a simple ring manufactured by injection molding from a type of polymer preferably from polypropylene, and configured to fit over splittable sheath 59. For example, the outer diameter of ring 50 may generally be in the range of 3 to 10 mm, preferably about 6 mm, and its width may generally be in the range of 0.2 to 10 mm, preferably about 4 mm.

Secured splittable introducer 57 is preferably configured to provide a slender passage 58 adapted to provide sealable passage therethrough for a catheter device (4, shown in FIG. 5F) which may be accessed via a tapering passage 55. Tapering passage 55 provided at the proximal end of slender passage 58 may be formed in a shape of, or comprise (e.g., manufactured by heat forming from of suitable polymer), a conical passage the tapering end of which is adapted to tightly fit over the outer surface of the catheter device (4) passing therein.

Secured splittable introducer 57 may be conveniently used to insert splittable sheath 59 into the body of the treated subject (not shown) by using conventional methods, by means of removable needle 3, as demonstrated in FIG. 5E. Needle 3 may be a conventional needle comprising a piercing tip 3b and needle handle 3a. After the insertion step catheter device 4 may be inserted through slender passage 58 and sheath 59 via tapering passage 55 of introducer 57, as demonstrated in FIG. 5F.

FIGS. 5B to 5D demonstrate splitting secure splittable introducer 57 which is initiated by fixating ring 50 and pushing splitting tabs, 51a and 51b, towards said ring 50. As demonstrated in FIGS. 5B and 5C, pushing splitting tabs, 51a and 51b, towards ring 50 splits the portion of introducer 57 between shanks 52a and 52b, and in turn causes the distal edge of detaching members, 53a and 53b, to push ring 50 distally and thereby break detachable connectors, 54a and 54b. As demonstrated in FIG. 5D, pulling splitting tabs, 51a and 51b, laterally in opposite directions cause gradual retraction of portions of sheath 59 via a central aperture (e.g., 92, in FIG. 9A) of ring 50 and concurrent split thereof. Tapering passage 55 may also be splittable and it may be an integral part of introducer 57, or alternatively, it may be a separate element reversibly attached thereto.

Ring 50 may be configured to allow removal thereof, as exemplified by removable securing ring 90, or removable securing device 125a or 125b, shown in FIGS. 9A-9C, and 12A-12b and 12C-12D, respectively.

Figure 6A:
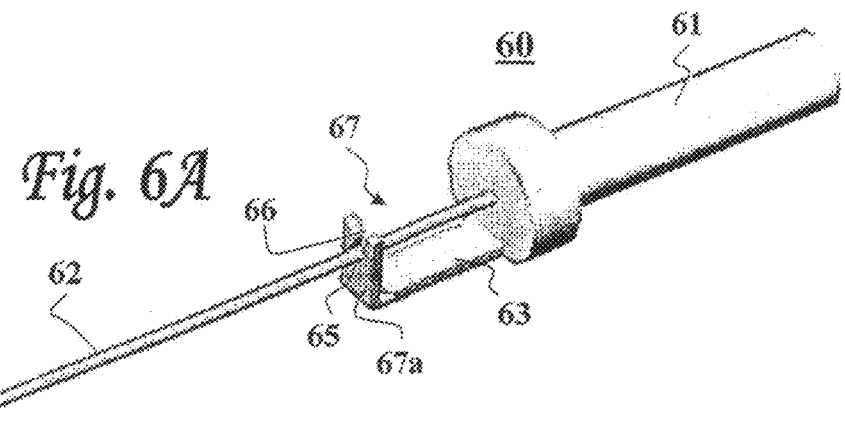
FIG. 6A is a perspective view of a piercing needle assembly of the invention comprising an integral removable adapter.

FIG. 6A is a perspective view of a piercing needle assembly 60 of the invention which comprises an integral detachable adapter 67 and a conventional piercing needle 62 attached to needle handle 61 thereof. Detachable adapter 67 comprises arm 67a connected to needle handle 61 by adapter base 63. While needle handle 61, adapter base 63 and arm 67a, may be connected in various ways (e.g., by gluing, welding, etc.), in a preferred embodiment of the invention they are formed as an integral unit. Adapter arm 67a is preferably perpendicular to adapter base 63, and it comprises an aperture 65 configured to receive needle sheath 103 of introducer 100, via slit 66 provided at its upper side.

Figure 6B:
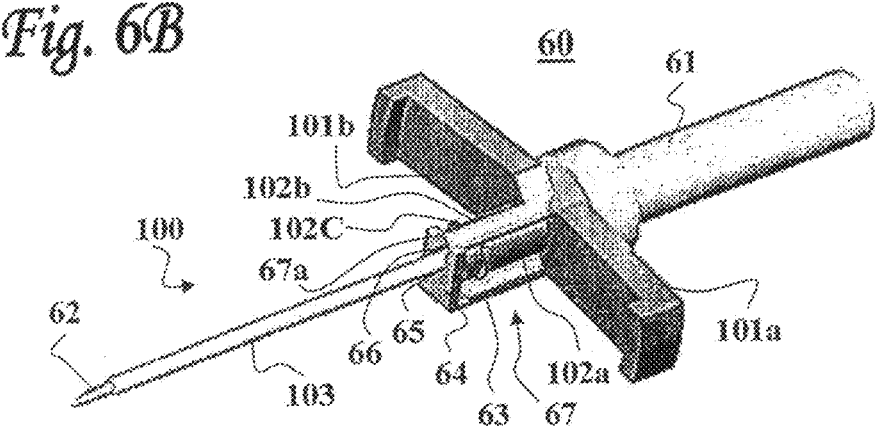
FIG. 6B demonstrates mounting the splittable introducer into the piercing needle assembly shown in FIG. 6A.

FIG. 6B demonstrates mounting splittable introducer 100 on piercing needle assembly 60. As seen, the gap between needle handle 61 and adapter arm 67a is designed to receive shanks 102a and 102b of introducer 100 therebetween. Splittable introducer 100 may be mounted on piercing needle assembly 60 by pulling needle 62 outwardly from aperture 65 via slit 66 and inserting it into splittable sheath 103 of introducer 100 and thereafter pushing needle 62, contained in splittable sheath 103, back into aperture 65 via slit 66. In this state the splittable introducer may be introduced into the body of the treated subject in a conventional way. After insertion of splittable sheath 103 into the body of the treated subject, piercing needle 62 can be removed by detaching adapter base 63 from adapter arm 67a, as demonstrated in FIG. 6C.

Figure 6C:
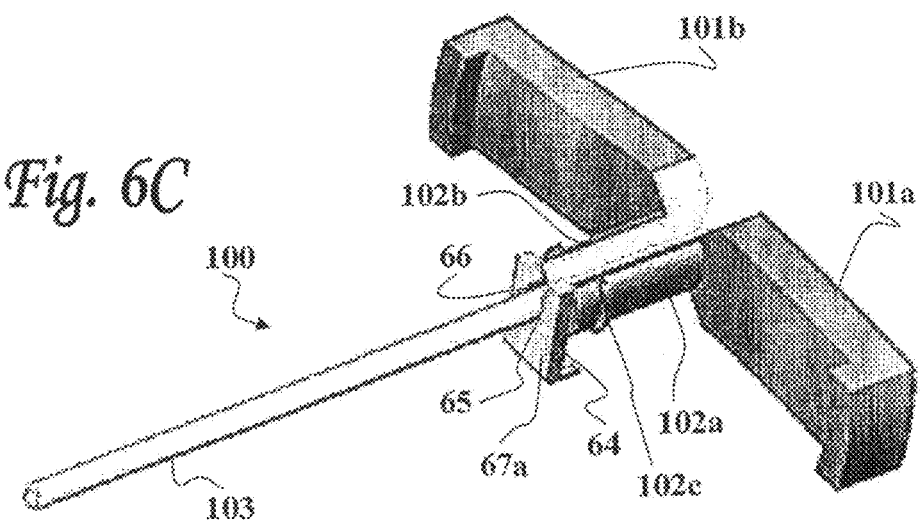
FIG. 6C shows the assembly shown in FIG. 6B after removal of the piercing needle.

As demonstrated in FIG. 6C, after removing piercing needle adapter arm 67a remains attached over splittable sheath 103, thereby preventing accidental splitting thereof. In this state a catheter device (not shown) may be inserted into the body of the treated subject via splittable sheath 103, which may be conveniently split by laterally pulling splitting tabs, 101a and 101b, as was previously described hereinabove. During the process of splitting sheath 103 adapter portions thereof are gradually retracted via aperture 65 of arm 67a and concurrently split until the entire sheath 103 is retracted from the body of the treated subject and split. Thereafter, adapter arm 67a may be removed by removing catheter device from aperture 65 via slit 66.

Needle handle 61, adapter base 63 and arm 67a, of piercing needle assembly 60 may be manufactured by injection molding from a type of polymer, such as but not limited to, polycarbonate. In a preferred embodiment the length of base 63 is generally in the range of 5 to 25 mm, preferably about 12 mm, and the diameter of aperture 65 is generally in the range of 3 to 10 mm, preferably about 6 mm. Base 63 can be made detachable, for example, by making it in a suitable thickness (e.g., about 0.2 mm) for allowing it to be easily ripped by the user by pulling and/or twisting needle handle 61.

FIG. 7A is a perspective view of a removable adapter 70 of the invention which comprises lateral fasteners, 71a and 71b. Removable adapter 70 is generally formed in a "U"-like shape having a distal arm 72 connected by base 73 to lateral fasteners 71a and 71b. As best seen in FIG. 7B, arm 72 comprises an aperture 75 adapted to receive sheath 103 of introducer 100, as exemplified in FIG. 7D. As best seen in FIG. 7C, base 73 may comprise distal portion 73a which is angled (θ, 15° to 60°) relative to proximal portion 73b thereof. Lateral fasteners, 71a and 71b, preferably comprise snaps, 78a and 78b, respectively, for holding splitting tabs, 101a and 101b, respectively, when splittable introducer 100 is fitted thereinto.

Aperture 75 may be accessed via slit 76 passing from the upper side of distal arm 72. The width of slit 76 is preferably designed to prevent the exit of sheath 103 passing through aperture 75 therefrom, while allowing the removal of catheter device therefrom. For example, the diameter of aperture 75 may generally be in the range of 0.5 to 5 mm, preferably about 1.6 mm, and the width of slit 76 may generally be in the range of 0.2 to 4 mm, preferably about 1.5 mm. In general, the width of slit 76 may be about 0.1 mm less then the outer diameter of the catheter device.

Removable adapter 70 is particularly useful in applications wherein opening 104 of splittable introducer needs to be accessed directly. For example, removable adapter can be used with conventional piercing needles that are designed to be received in introducer 100 such that their distal piercing tip can protrude outwards via the distal end of sheath 103. Removable adapter 70 may be manufactured using similar methods and materials as previously described hereinabove with reference the removable adapters shown in FIGS. 1A-1D. The gap between lateral fasteners, 71a and 71b, is generally in the range of 5 to 20 mm, preferably about 12 mm.

Figures 8A, 8C:
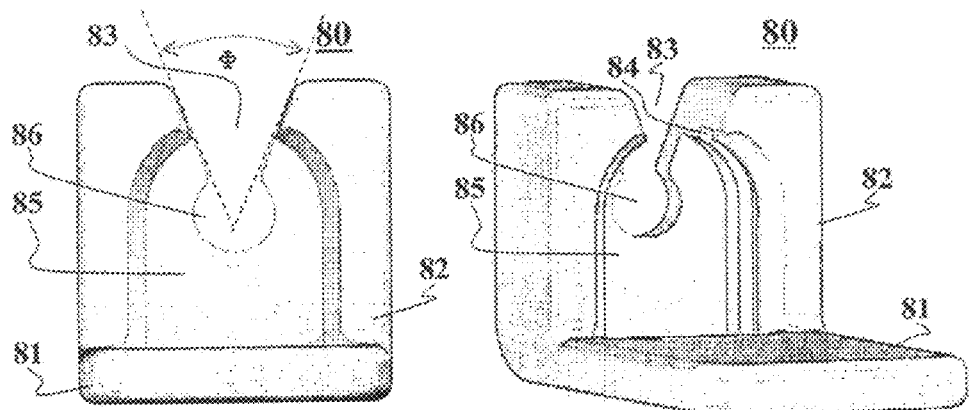
FIGS. 8A and 8B are perspective views of a removable securing device of the invention comprising an attachment surface.
FIG. 8C is a rear view of the removable securing device shown in FIGS. 8A and 8B.
Figure 8B:
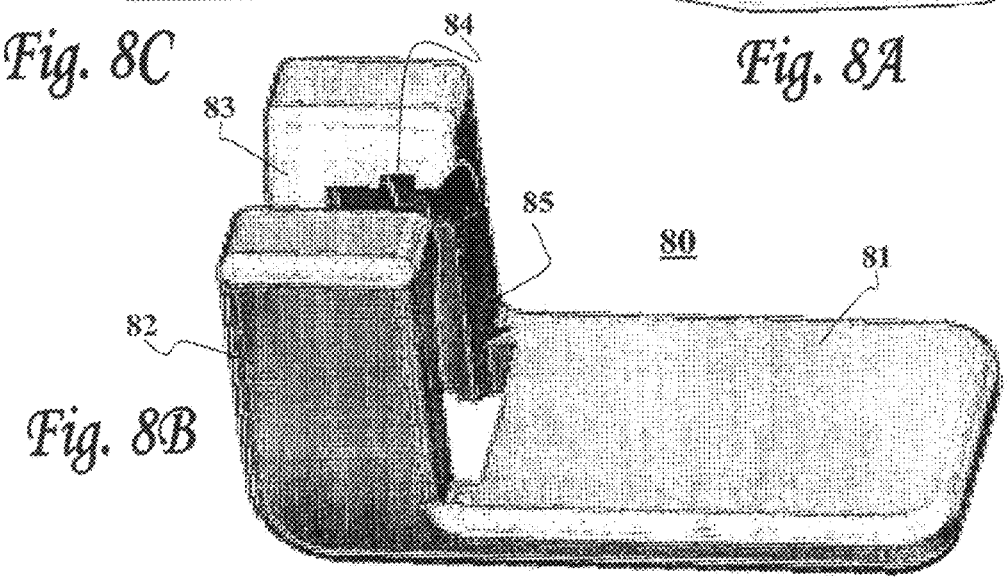

FIGS. 8A and 8B are perspective views of a removable securing device 80 of the invention comprising an attachment surface 81. Removable securing device 80 comprises arm 82 to which attachment surface 81 is attached in a right angle. Attachment surface 81 is used to prevent discomfort of the treated patient which may be caused when pressing connector 80 to the patient's body, by enlarging the surface area to which the pressure is applied.

Figure 8D:
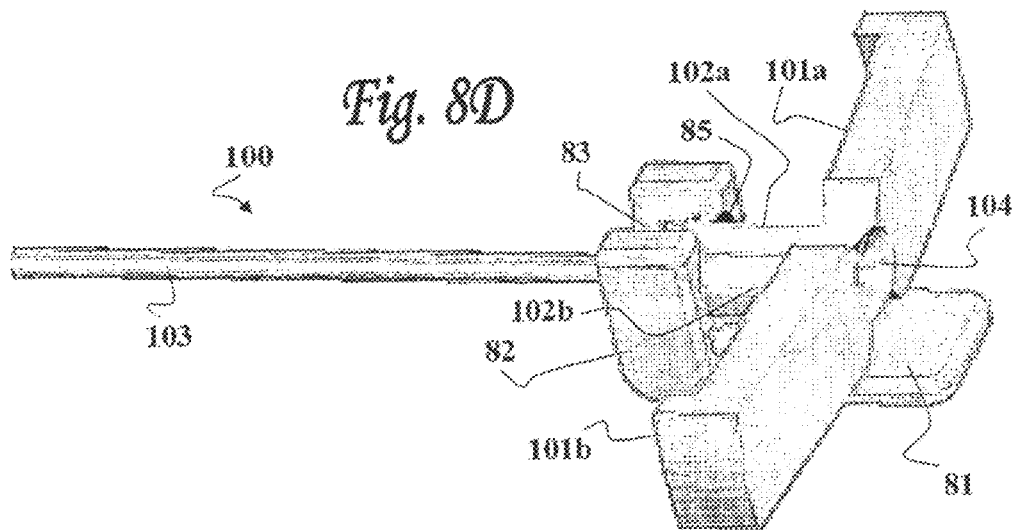
FIG. 8D demonstrates assembling a splittable introducer into the removable securing device shown in FIGS. 8A-8C.

As best seen in FIG. 8C, arm 82 comprises an aperture 86 configured to receive and hold splittable sheath 103 of introducer 100 and prevent splitting thereof during use in the body of the treated subject. Aperture 86 may be accessed via opening 83 which passes from the upper side of arm 82 and terminates in said aperture 86. Arm 82 further comprises a fastening recess 85 which is designed to receive the distal ends of shanks, 102a and 102b, therein, as demonstrated in FIG. 8D. Inner face of recess 85 may comprise grooves 84 configured to receive respective flanges 102c (Shown in FIG. 3B) formed near the distal ends of shanks 102a and 1021b.

The steps of inserting the splittable sheath 103 into the body of the treated subject, inserting catheter device and removal of splittable introducer 100 and removable adapter are substantially similar to the steps previously described hereinabove with reference to FIGS. 1A-1D, 2A-2B, and 3A-3B, and thus will not be described now again for the sake of brevity.

Removable adapter 80 may be manufactured using similar methods and materials as previously described hereinabove with reference to FIGS. 1A-1D. The length of attachment surface 81 is generally in the range of 10 to 30 mm, preferably about 15 mm, and the diameter of aperture 86 is generally in the range of $OD_{cath}$−0.1 to $OD_{cath}$+0.1 mm wherein $OD_{cath}$ is the outer diameter of the catheter. The height of arm 82 is generally in the range of 5 to 15 mm, preferably about 8 mm, and its width is generally in the range of 4 to 12 mm, preferably about 6 mm. The angle Φ of opening 83 may generally be in the range of 15° to 60°, preferably about 30°.

FIG. 9A is a front view of a removable securing ring 90 of the invention which is designed to prevent splitting of a splittable sheath 103 of introducer 100 in the body of the treated subject, and for facilitating splitting thereof while it is removed from the body of the treated subject. Removable securing ring 90 comprise aperture 92 configured to receive and hold splittable sheath 103 therein, and radial slit 91 which passes along a radius of removable securing ring 90.

FIG. 9B demonstrates splitting of a splittable introducer 100 being held by removable securing ring 90. As in the previously described examples, in this operation splitting tabs, 101a and 101b, are pulled laterally and consequently shanks, 102a and 102b, are split and portions of splittable sheath 103 are retracted proximally via aperture 92 and concurrently split.

After the entire length of splittable sheath 103 is retracted and split the splittable introducer is removed. Removable securing ring 90 may be removed by pulling radial sides of slit 91 in opposing axial directions, as demonstrated in FIG. 9C, thereby forming a gap between the radial sides of slit 91 through which catheter device 4 may be removed.

FIGS. 10A and 10B demonstrates a removable adapter 10' of the invention that is suitable to be used with a catheter cutter device 111 (FIG. 10B) and with a splittable introducer 100 (FIG. 10A). In FIG. 10A removable adapter 10' is operatively attached to catheter insertion device 105 via connector 14 and catheter device 4 is advanced via slender passage element 110 provided in the tapering end of flexible sleeve 107 of catheter insertion device 105 into the body of the treated subject (not shown) through splittable sheath 103. Catheter 4 is advanced by gripping portions thereof and pushing them distally which presses resilient/elastic section 108 (e.g., bellow) of sleeve 107. After completing the insertion of catheter device 4, flexible sleeve 107 may be teared by pulling tearing tab 106 upwardly and tearing flexible sleeve 107 along tearing lines 109. Thereafter, splittable introducer 100 may be split and removable adapter 10' may be removed in a similar fashion as was previously described hereinabove with reference to FIGS. 1A-1D.

FIG. 10B demonstrates trimming the length of catheter device 4 prior to insertion thereof into the body of the treated subject by means of catheter cutter 111 fitted into the gap provided between the arms of removable adapter 10'. Cutter device 111 is fitted in removable adapter 10' such that a portion of catheter 4 can be passed via a passage (not shown) provided therein, wherein said passage is aligned with the apertures provided in the arms of removable adapter 10'. The catheter portion passed via the passage of cutter device 111 can be then trimmed by pushing blade 112 downwardly. Thereafter, the cutter device is removed and the splittable introducer is snapped into removable adapter as shown in FIG. 10A.

FIGS. 11A to 11C show a removable slender passage 130 suitable for use with the devices of the invention. Slender passage 130 may have, but not limited to, a cross cross-sectional shape, and it comprises a tapering passage (not shown) provided between distal slender opening 130b and a proximal opening 130c thereof. FIGS. 11A and 11B show removable slender passage 130 mounted over opening 104 of splittable introducer 100. As shown, catheter device 4 passes via slender passage 130 and it is then received inside sheath 103 of splittable introducer 100 via its distal opening 104. FIG. 11C shows removable slender passage 130 after removing splittable introducer 100. Removable slender passage 130 may be removed by pressing, or pulling laterally, opposing wings, 131a and 131b, thereof and widening slit 130a to form a passage suitable for removing catheter device 4 therefrom.

Removable passage 130 may be manufactured by injection molding from flexible polymer, such as silicone or neoprene. The length of removable slender passage 130 is generally in the range of 1 to 5 mm, preferably about 2 mm, and the diameter of its proximal opening 130c is generally in the range of 0.5 to 4 mm, preferably about 2 mm.

Figure 12A:
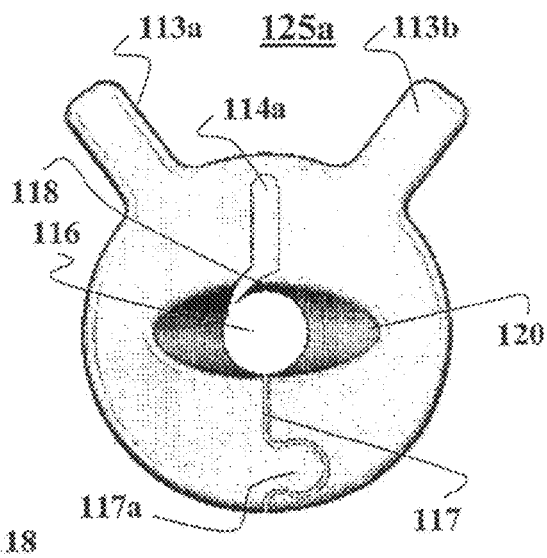
FIGS. 12A and 12B are front and rear views, respectively, of a removable securing device of the invention comprising a lower slit and locking mechanism.
Figure 12B:
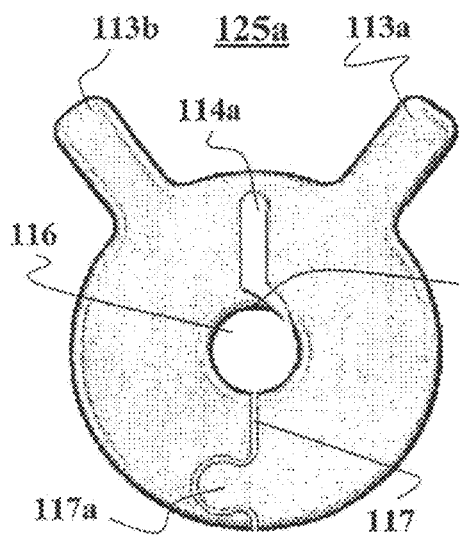

FIGS. 12A and 12B are front and rear views, respectively, of a removable securing device 125a of the invention comprising a lower slit 117 and locking mechanism 117a. Removable securing device 125a is formed in a ring like shape and it comprises a central aperture 116 and a radial hollow passage 114a which accesses aperture 116 and terminates near the outer circumference of removable securing device 125a. Removable securing device 125a further comprises releasing tabs 113a and 113b provided at its upper side in substantially equal distances from radial hollow passage 114a. The front face of removable securing device 125a comprises an elliptic recess 120 comprising central aperture 116, wherein the line connecting the centers (not shown) of said elliptic recess 120 is perpendicular to at least open radial section 114a and/or slit 117.

Figure 12C:
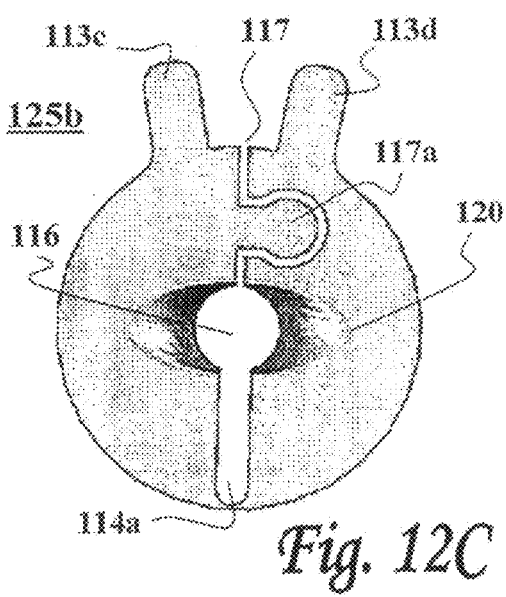
FIGS. 12C and 12D are front and rear views, respectively, of a removable securing device of the invention comprising an upper slit and locking mechanism.
Figure 12D:
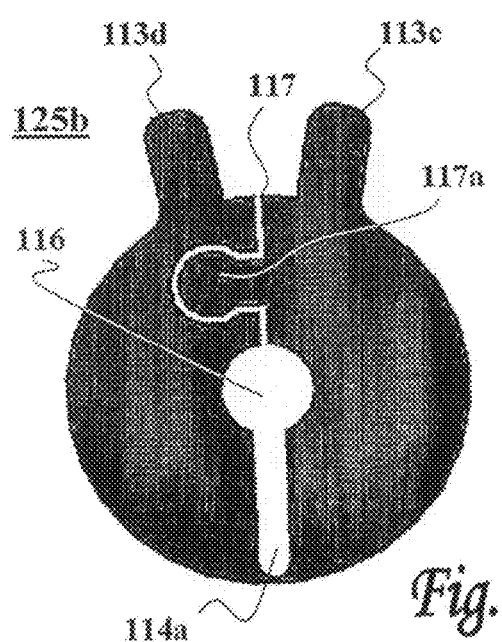

FIGS. 12C and 12D are front and rear views, respectively, of a removable securing device 125b of the invention comprising an upper slit 117 and locking mechanism 117a. Removable securing device 125b is formed in a ring like shape and it comprises a central aperture 116 and a radial hollow passage 114a which accesses aperture 116 and terminates near the outer circumference of removable securing device 125a. Removable securing device 125b further comprises releasing tabs 113c and 113d provided at its upper side in substantially equal distances from slit 117. The front face of removable securing device 125b comprises an elliptic recess 120 comprising central aperture 116, wherein the line connecting the centers (not shown) of said elliptic recess 120 is perpendicular to at least open radial section 114a and/or slit 117.

Releasing tabs 113a and 113b are used to facilitate removal of removable securing device 125a by pressing them one towards the other, thereby opening locking mechanism 117a. Similarly, releasing tabs 113c and 113d are used to facilitate removal of removable securing device 125b by pulling them laterally, thereby opening locking mechanism 117a. Furthermore, releasing tabs 113a and 113b also prevents rotations of removable securing device 125a about the catheter device 4 passing via central aperture 116 (shown in FIG. 12F) and improve the hand grip on the device, thereby improving the control of the insertion procedure.

Figure 12F:
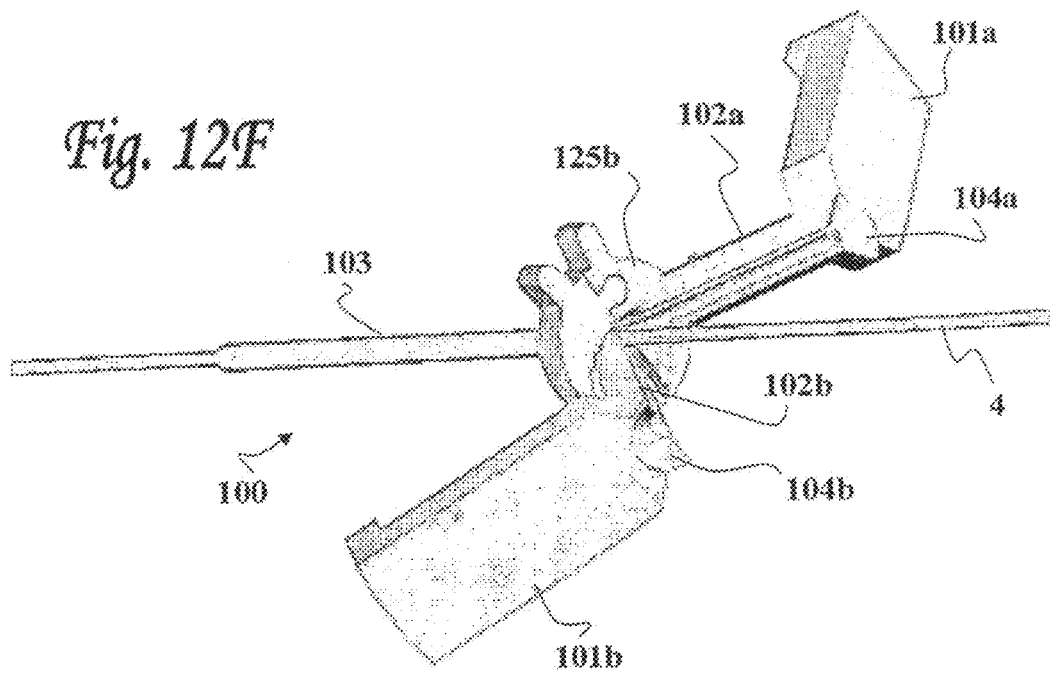

FIGS. 12E, 12F, and 12G, are front perspective, rear perspective, and side, views, respectively, demonstrating splitting a splittable introducer 100 secured by the removable securing device 125b. As seen, splittable introducer 100 is split by laterally pulling splitting tabs, 101a and 101b, thereof, thereby splitting the shanks section, 102a and 102b, and detaching removable securing device 125b from the distal tips of shanks 120a and 120b. Further pulling splitting tabs, 101a and 101b, retracts further portions of sheath 103 via aperture 116, wherein said portions of sheath 103 are split as they emerge via aperture 116 into elliptic recess 120, as best seen in FIGS. 12F and 12G. In this way the split portions of sheath 103 are pressed into lateral grooves formed by elliptic recess 120 and thereby centers removable securing device 125b, and preventing rotation thereof, about sheath 103.

Figure 12I:
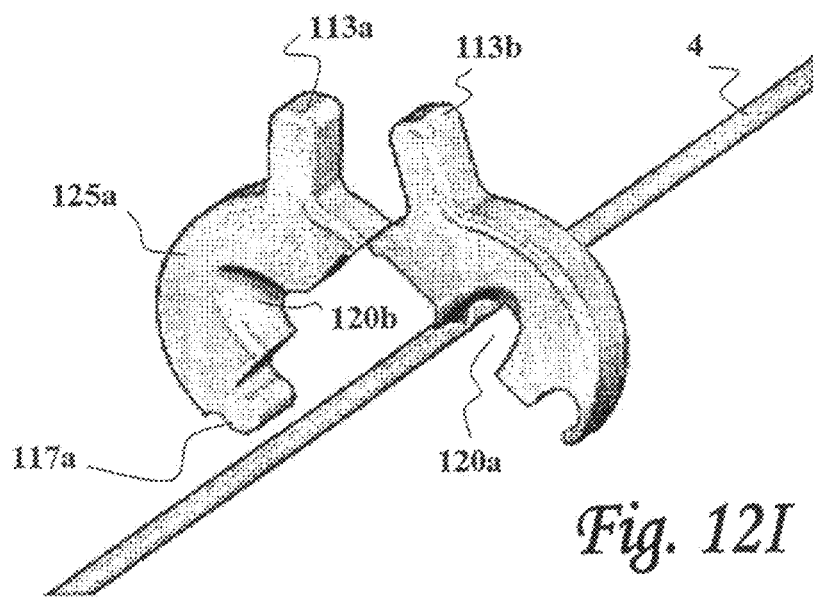
FIG. 12I demonstrates removal of the removable securing device

FIG. 12H shows removable securing device 125b and catheter device 4 passing therethrough after removal of the splittable introducer 100. FIG. 12I demonstrates removal of the removable securing device 125a. As seen, removable securing device 125a may be removed by pressing releasing tabs, 113a and 113b, one towards the other, thereby opening locking mechanism 117a and splitting removable securing device 125a along slit 117 and radial hollow passage 114a. Of course, removal of removable securing device 125b can be performed in a similar fashion by pulling laterally its releasing tabs, 113c and 113d, in opposing directions.

Radial hollow passage 114a may end in a stopper portion 118 which provides a slim passage therefrom into aperture 116. In this way entrance of splittable portions into radial hollow passage 114a may be prevented. Stopper portion 118 is preferably an integral part of removable securing device 125b formed as part of the circumferential rim of aperture 116.

FIG. 13 is a perspective view of a removable securing device 138 of the invention that is configured to receive a needle guard (144, in FIG. 14B). Removable securing device 138 comprises a base 137 and an arm 132 which comprises an aperture 136 adapted to receive sheath (103) of an introducer (100). Base 137 may comprise distal portion 137a which is angled (e.g., 15° to 60°) relative to proximal portion 137b thereof. The proximal face of arm 132 comprises a gripping groove 135 adapted to receive the distal tips of shanks (102) of an introducer (100). Aperture 136 may be accessed via opening 133 passing in the upper side of arm 132.

The distal side of arm 132 is configured to receive a needle guard (144), as exemplified in FIG. 14B. Slit 133 allows fitting sheath (103) of an introducer (100) into aperture 136 therethrough, and removal of a catheter device passing therethrough after removal of said introducer. As in the previously described embodiments shown in FIGS. 1-2 and 7, the angled distal portion of base 137 renders the steps of piercing the tissues of the treated subject and introducing the splittable sheath 103 into its body easier for the user, by allowing said user to conveniently introduce a piercing needle place in the introducer in a suitable angle for insertion.

Removable securing device 138 may be manufactured by injection molding from a type of polymer, such as but not limited to, polypropylene. The width of base 137 may generally be in the range of 8 to 25 mm, preferably about 12 mm. The length of proximal portion 137*b* may generally be in the range of 2 to 10 mm, preferably about 6 mm, and the length of distal portion 137*a* may generally be in the range of 2 to 25 mm, preferably about 15 mm. The diameter of gripping groove 135 may generally be in the range of 2 to 8 mm, preferably about 4 mm, and the diameter of aperture 136 may generally be in the range of 0.1 to 8 mm, preferably about 2 mm. The width of opening 133 is configured to allow passage of an introducer sheath, and the removal of catheter device therethrough. For example, the width of opening 133 may generally be in the range of 0.1 to 5 mm, preferably about 1 mm.

FIG. 14A is a perspective view of a removable adapter 140 of the invention that is configured to receive a needle guard (144, in FIG. 14B). Removable adapter 140 is generally formed in a "U"-like shape having a distal arm 142 connected by base 141 to lateral fasteners 147*a* and 147*b*. Arm 142 comprises an aperture 146 adapted to receive sheath 103 of introducer 100, as exemplified in FIG. 14B. Base 141 may comprise distal portion 141*a* which is angled (e.g., 15° to 60°) relative to proximal portion 141*b* thereof. Lateral fasteners, 148*a* and 148*b*, preferably comprise snaps, 148*a* and 148*b*, respectively, for holding splitting tabs (101*a* and 101*b*) when splittable introducer (100) is fitted thereinto.

Aperture 146 may be accessed via opening 143 passing in the upper side of distal arm 142. The width of opening 143 is preferably designed to prevent the exit of sheath 103 passing through aperture 146, while allowing the removal of catheter device therefrom. For example, the diameter of aperture 146 may generally be in the range of 0.5 to 5 mm, preferably about 1.6 mm, and the width of opening 143 may generally be in the range of 0.2 to 4 mm, preferably about 1.5 mm. In general, the width of opening 143 may be about 0.1 mm less then the outer diameter of the catheter device.

FIG. 14B is a perspective view of the removable adapter 140 shown in FIG. 14A shown with a splittable introducer 100 including a piercing needle 3 assembly, and a needle guard 144 covering the needle 3*b*. Removable adapter 140 may be manufactured by injection molding from a type of polymer, such as but not limited to, polypropylene. The geometrical dimensions of the proximal and distal portions, 141*b* and 141*a*, respectively, and of arm 142, may be substantially the same as of the corresponding elements of removable adapter 138 described above with reference to FIG. 14A. Preferably, the gap between lateral fasteners, 148*a* and 148*b*, is in the range of 5 to 25 mm, preferably about 15 mm, and the base 141 is formed in a tapering shape which width is gradually reduced towards its distal end, to which arm 142 is attached.

It should be noted that the removable adapter and securing means of the invention also substantially minimize in and out movements of the catheter device during the splitting of the splittable introducer. This advantageous result is obtained since there is no need to retract portions of the catheter device from the body of the treated subject before splitting the introducer. The removal of conventional splittable introducer (without the adapter means of the invention) requires retraction of portions of the catheter device which are introduced back into the body of the treated subject after splitting the introducer. This result advantageously reduces the chances of causing an infection during the catheter insertion procedure.

The removable adapter of the invention may further comprise a self-adhering strip (not shown) attached to the base (22, 32, 45*c*, 63, 73, 137, in FIGS. 2-4, 6-7 and 13), or the attachment surface (81, in FIG. 8A), of the adapter, wherein said self-adhering strip is covered by a removable cover, which may be removed by the user after completing insertion of the splittable introducer into the body of the treated subject, for attaching the removable adapter therewith to the body of said subject.

According to another preferred embodiment of the invention the removable adapter 121 is configured to receive the splittable sheath 103 of the splittable introducer 100 via a slit 121*e* formed in a bottom section of the removable adapter, as shown in FIGS. 15A to 15F. Removable adapter 121 has a "U"-like shaped portion comprising a distal arm 121*a* and a proximal arm 121*b* connected by a base 121*f*. Quick connecting means 124 and 122 may be provided on the outer sides of the distal 121*a* and proximal 121*b* arms, respectively. Proximal arm 121*b* and proximal quick connecting means 124 comprise respective slits, 121*g* and 124*g*, passing from their upper sides towards a common central bore provided therein, wherein said slits provide a path for releasing the catheter tube (not shown) passed through said central bore and removing adapter 121 after completing the insertion procedure, as was previously described with reference to FIGS. 1A to 1D.

The base 121*f* of the "U"-like shaped portion of removable adapter 121 may comprise an angled section such that its distal side is elevated relative to its proximal side. Distal arms 121*a* and the quick connector 122 provided thereon comprise a common slit 122*g* passing from their bottom sides towards a common central bore provided therein, wherein said slit 122*g* connects to slit 121*e* passing along a distal portion of base 121*f*. Lateral opening 121*o* provided in base 121*f* allows placing a splittable introducer 100 in removable adapter 121 by passing the splittable sheath 103 via lateral opening 121*o* into slit 121*e* and then "snapping" it via slit 122*g* into the central bore provided in distal arm 121*a* and distal quick connector 122. In a similar way, slits 122*g* and 121*e* and lateral opening 121*o* are advantageously used for releasing the catheter tube (not shown) passed through said central bore and removing adapter 121 after completing the insertion procedure.

Distal arm 121*a* further comprises upper fastening means 121*d* for holding the distal portions of shanks 102*a* and 102*b* of splittable introducer 100 when placed therein. In this way splittable introducer is securely placed in removable adapter 121 by passing its splittable sheath through lateral opening 121*o* and slits 122*g* and 121*e*, pressing the distal portion of shanks 102*a* and 102*b* against distal arm 121*a* and pushing splitting tabs 101*a* and 101*b* down towards base 121*f* to "snap" splittable sheath 103 into the central bore passing in distal arm 121*a* and distal quick connecting means 122, and simultaneously "snap" the upper sides of splitting tabs 101*a* and 101*b* via snaps 121*h* provided on the upper portion of the inner side of proximal arm 121*b*.

FIGS. 15D and 15E show removable adapter 121 comprising splittable introducer 100, securely fitted therein. As can be seen in this preferred embodiment the splittable introducer is held firmly by the removable adapter 121, which provides the user better control of the splitting process and prevents accidental release over splittable introducer 100 from removable adapter 121. Removable adapter 121 may be similarly designed to include other connecting means on its distal and proximal arms, or alternatively, with only one connecting means on its distal or proximal arm, or without any connecting means at all.

FIG. 15F shows removable adapter 121 comprising splittable introducer 100 assembled therein, a needle cover 127 connected over quick connecting means 122 (shown in FIGS. 15A-15E), and a cap 128 connected over quick connecting means 124.

In another preferred embodiment of the invention, shown in FIGS. 16A to 16E, the design of the removable adapter 160 includes enclosing means 161 configured to securely hold splittable sheath 103 and to allow easy and convenient mechanism for placing the splittable introducer 100 in removable adapter 160, while minimizing the risks of damaging the splittable introducer, and eliminating accidental release thereof from removable adapter.

Removable adapter 160 has a "U"-like shaped portion comprising a distal arm 121k (shown in FIG. 16B) and a proximal arm 121b connected by a base 121f. Quick connecting means 124 may be provided on the outer side of proximal arm 121b. Proximal arm 121b and proximal quick connecting means 124 comprise respective slits, 121g and 124g, passing from their upper sides towards a common central bore provided therein, wherein said slits provide a path for releasing the catheter tube (not shown) passed through said central bore and removing adapter 160 after completing the insertion procedure, as was previously described hereinabove.

Enclosing means 161 is attached to distal arm 121k, and it may be advantageously formed in a shape of a quick connecting means to provide the same connectivity as exemplified in the previously described embodiments (e.g., quick connecting means 122 in FIG. 15A). Enclosing means 161 preferably comprise a base section 161f attached to distal arm 121k, and a fastening section 161e. Fastening section 161e preferably connects to base section 161f by means of a hinge 164 (shown in FIG. 16B) (e.g. a thin strip of flexible material), such that it is partially rotatable about said hinge between an "open" state (shown in FIGS. 16B and 16D) and a "closed" state (shown in FIGS. 16A, 16C and 16E). Base section 161f and fastening section 161e comprise respective grooves, 165f and 165e (shown in FIG. 16B), passing along their length such that a bore 165 (shown in FIG. 16A) is formed therebetween when fastening section 161e is moved to the "closed" state, e.g., with the assistance of tab 161b.

Base section 161f and fastening section 161e may advantageously comprise holding tabs 161a (shown in FIGS. 16A and 16C), wherein said holding tabs 161a are adapted to hold the distal portions of shanks 102a and 102b after placing splittable introducer in removable adapter 160 and fastening section 161e is moved the "closed" state.

Figure 16C:
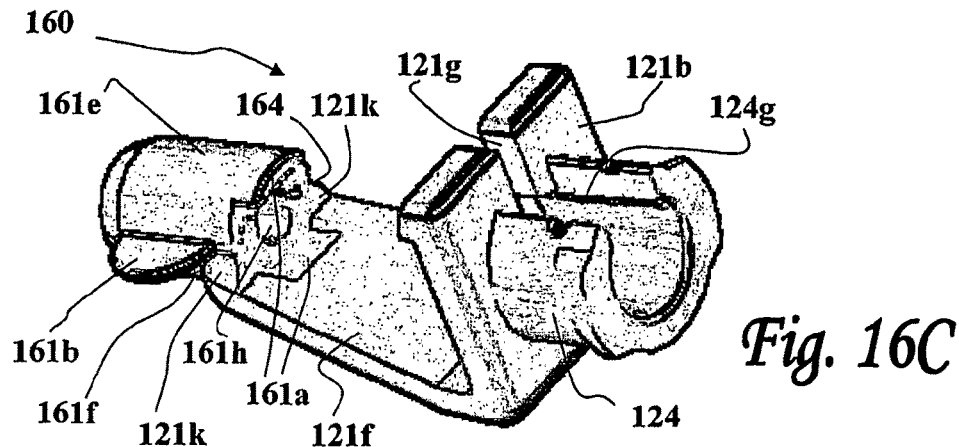
Figure 16D:
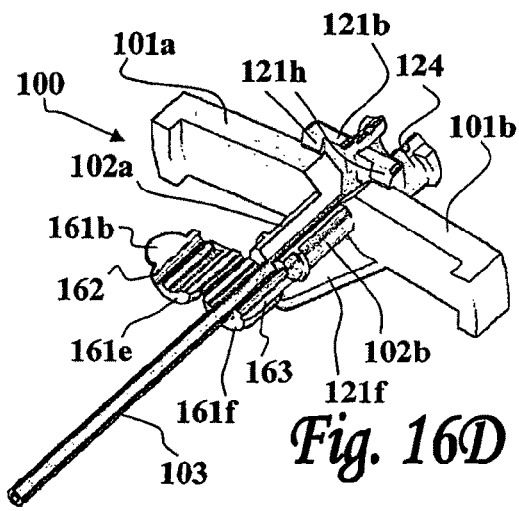
Figure 16E:
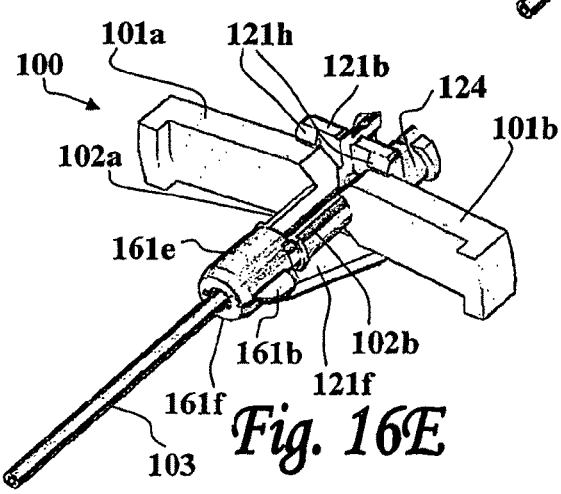

A locking mechanism is conveniently used to fasten fastening section 161e over base section 161f. For example, with reference to FIG. 16A, base section 161f may comprise a longitudinal projection 163 protruding laterally in the opposite direction of hinge 164, and fastening means 161e may comprise a respective longitudinal groove 162 adapted to fit over longitudinal projection 163 when in the "closed" state. In this way splittable introducer 100 may be conveniently assembled in removable adapter 160 by opening fastening section 161e and placing splitting tabs 101a and 101b and shanks 102a and 102b in the gap between proximal arm 121b and distal arm 121k, such that splitting tabs 101a and 101b are placed beneath fasteners 121h and a proximal section of splittable sheath 103 is placed in groove 165f of base section 161f, as shown in FIG. 16D. After placing splittable introducer 100 in removable adapter 160 fastening section 161e is turned into the "closed", which may be then secured by the locking mechanism, for example, by pressing fastening section 161e against base section 161f and causing longitudinal projection 163 to engage in longitudinal groove 162, as demonstrated in FIG. 16E.

FIGS. 17A to 17H illustrate another preferred embodiment of the invention wherein the removable adapter 170 comprises proximal locking means 173. Removable adapter 170 has a "U"-like shaped portion comprising a distal arm 170a and a proximal arm 170b connected by a base 171. Quick connecting means 174 and 172 may be provided on the outer sides of the distal 170a and proximal 170b arms, respectively. Distal arm 170a and distal quick connecting means 172 comprise a common slit 172g passing from the upper side thereof until it connects to a common central bore passing in the distal arm 170a and distal quick connecting means 172, wherein said slit provide a path for releasing the catheter tube (not shown) passed through said central bore and removing adapter 170 after completing the insertion procedure, as was previously described hereinabove.

Quick connecting means 174 may be provided on the outer side of proximal arm 170b. Proximal arm 170b and proximal quick connecting means 174 comprise respective slits, 170g and 174g, passing from their upper sides towards a common central bore provided therein, wherein said slits provide a path for releasing the catheter tube (not shown) passed through said central bore and removing adapter 170 after completing the insertion procedure, as was previously described hereinabove.

Removable adapter 170 may comprise a twisting channel passing along the bottom sides of base 171 (channel 171c) and distal quick connecting means 172 (channel 172c), as shown in FIG. 17C. Twisting channel is provided for adding flexibility to removable adapter 170 and allowing the widening of slits 172g, 170g and 174g by bending base 171 along its longitudinal center 171s (shown in FIG. 17A), which facilitates the placing of the splittable introducer 100 in the removable adapter 170.

Figure 17D:
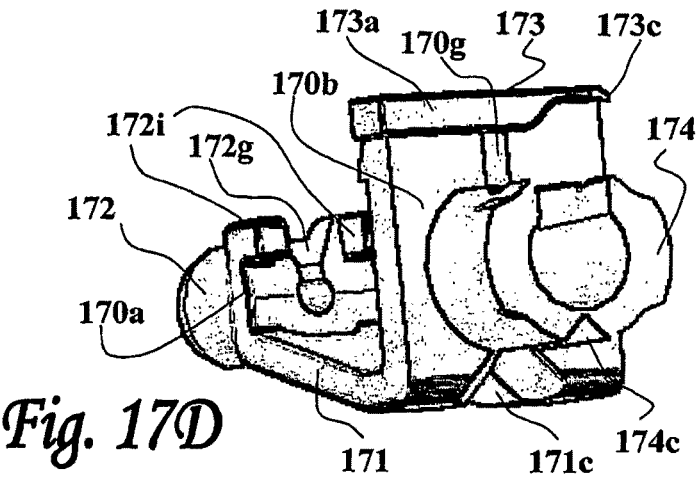
Figure 17E:
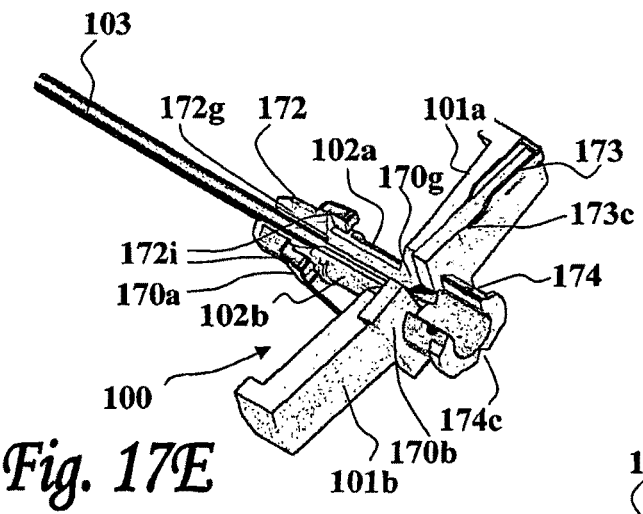
Figure 17F:
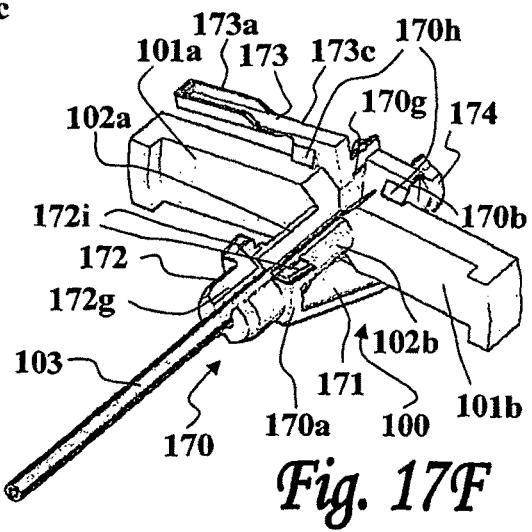
Figure 17G:
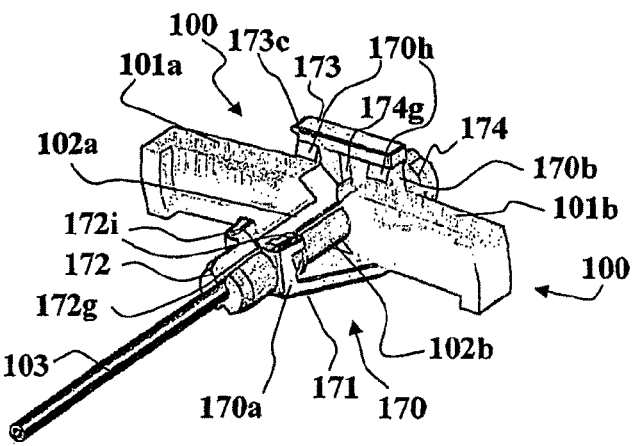
Figure 17H:
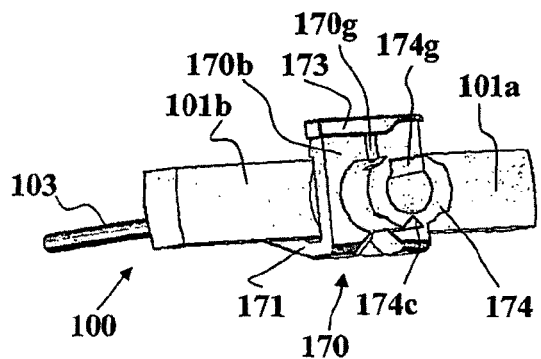

As can be seen in FIGS. 17E and 17F, splittable introducer 100 may be assembled in removable adapter 170 by sliding splittable sheath 103 through the central bore passing in distal arm 170a and distal quick connecting means 172, pressing the distal portion of shanks 102a and 102b against the inner side of distal arm 170a, such that they are held therein by fastening means 172i, and pressing splitting tabs 101a and 101b until they snap into adapter 170 and held by snaps 170h. In this state, base 171 slightly curves along central longitudinal line 171s such that slits 172g, 170g and 174g, widen.

After splittable introducer 100 is placed in removable adapter 170 it may be locked therein by means of locking mechanism 173 provided on proximal arm 170b. Locking mechanism 173 preferably comprise a locking arm attached to an upper side corner of proximal arm 170b by means of hinge 173c, such that it may be turned about said hinge 173c between an "open" (FIGS. 17A, 17B and 17E-17F) and "closed" (FIGS. 17C, 17D and 17G-17H) states. Locking mechanism 173 may comprise grasping walls 173a formed around portion of locking arm, wherein said grasping walls 173a are configured to fit over a portion of proximal wall 170b when moved the locking arm is turned to the "closed" state.

Locking mechanism 173 may be obtained by means of a lateral protrusion 170t (shown in FIGS. 17A-17B) formed on (or attached to) the upper corner of the portion of proximal wall covered by grasping walls 173a, wherein said lateral protrusion is configured to fit into a corresponding groove 173b (shown in FIG. 17A) provided in one of the grasping walls 173a, which is placed over said upper corner when in the "closed" state.

FIGS. 18A to 18G illustrate a removable adapter 180 of the invention having a movable proximal arm 180b. Removable adapter 180 has a "U"-like shaped portion comprising a distal arm 180a and a proximal arm 180b connected by a base 181.

Quick connecting means 184 may be provided on the outer side of proximal arm 180b. Proximal arm 180b and proximal quick connecting means 184 comprise respective slits, 181g and 184g, passing from their upper sides towards a common central bore provided therein, wherein said slits provide a path for releasing the catheter tube (not shown) passed through said central bore and removing adapter 180 after completing the insertion procedure, as was previously described hereinabove.

Distal arm 180a may comprise distal quick connecting means 182 comprising a common slit 182g passing from the upper side thereof until it connects to a common central bore passing in the distal arm 180a and distal quick connecting means 182, wherein said slit provide a path for releasing the catheter tube (not shown) passed through said central bore and removing adapter 180 after completing the insertion procedure, as was previously described hereinabove.

Figure 18A:
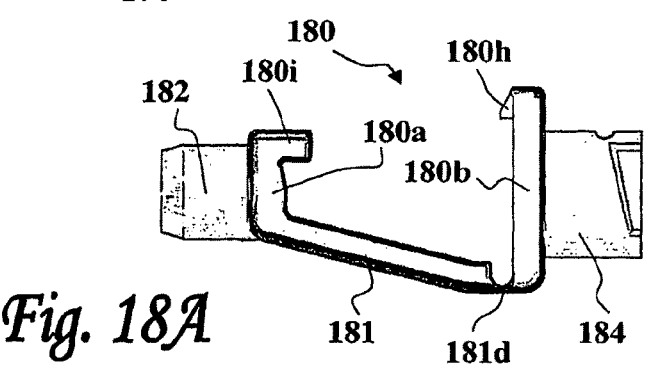
FIGS. 18A to 18G illustrate an embodiment of the removable adapter having a movable arm.
Figure 18B:
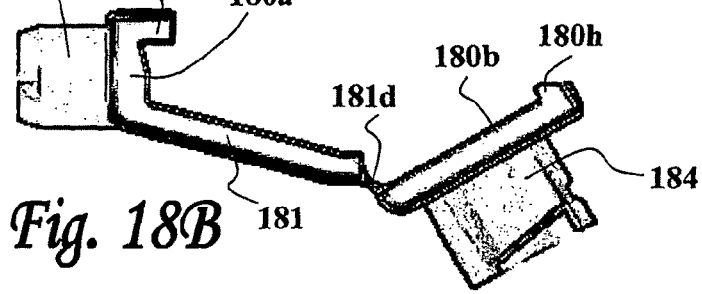
Figure 18C:
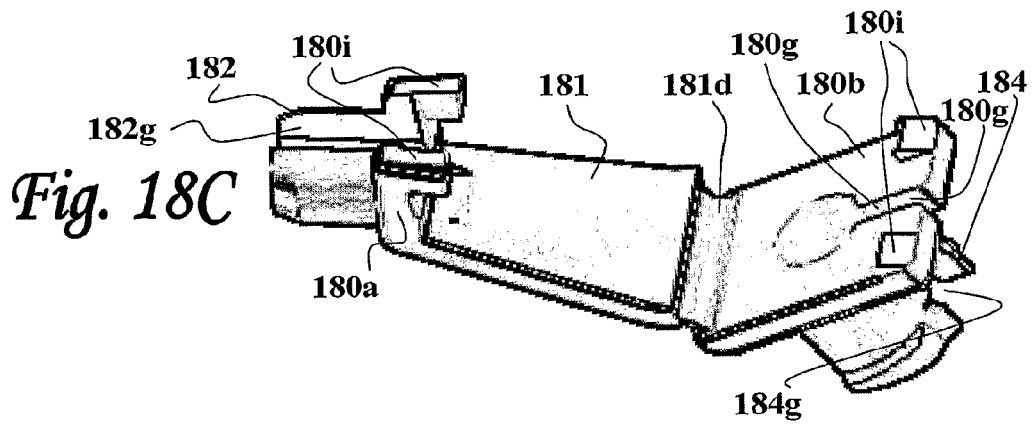
Figure 18D:
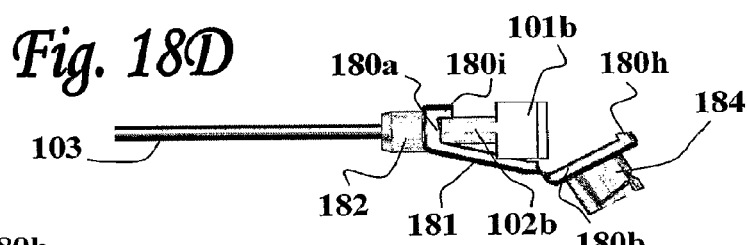
Figure 18E:
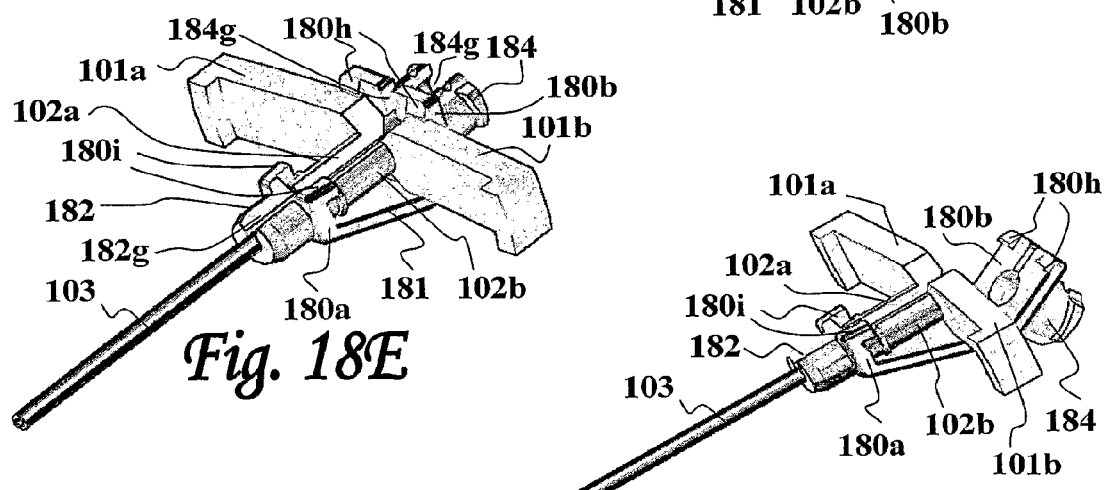
Figure 18G:
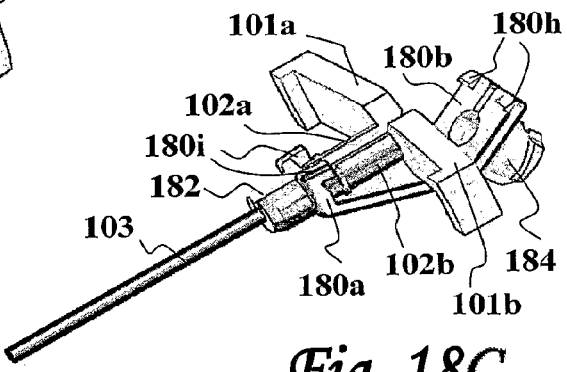
Figure 18F:
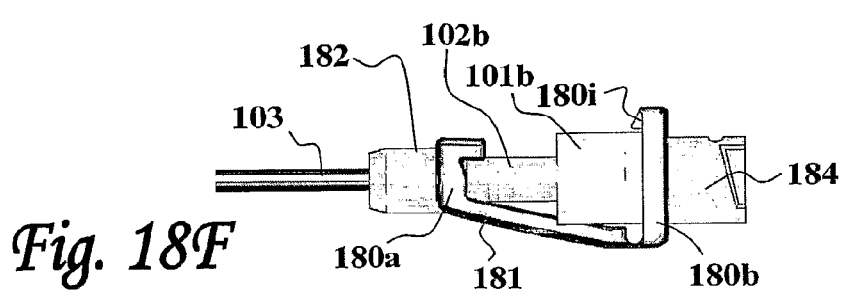

Proximal arm 180b is designed to be movable about a hinge 181d (e.g. a thin strip of flexible material) connecting it to the base 181. In this way splittable introducer 100 may be assembled in removable adapter 180 by passing its splittable sheath 103 through the central bore of distal arm 180a and distal quick connecting means 182, until the distal portion of shanks 102a and 102b is pressed against the inner side of distal arm 180a and held by fastening means 182i provided on distal arm 180a, as illustrated in FIGS. 18C-18D. After so placing splittable introducer 100 it may be locked therein by pushing proximal wall 180b distally until fasteners 180i provided on the upper inner side of proximal arm 180b clasp the upper side or splitting tabs 101a and 101b, as illustrated in FIGS. 18E and 18F. This mechanism simplifies the assembling of splittable introducer 100 and removable adapter 180, and prevents accidentally damaging splittable introducer 100 during the assembly steps.

The removable adapters described with reference to FIGS. 15 to 18, may be manufactured by the same processes and using the same materials as described herein above with reference to FIGS. 1-4 and 7-8. The dimensions of the elements shown in FIGS. 15-18 are substantially the same as in the similar elements in the previously described embodiments.

All of the abovementioned parameters are given by way of example only, and may be changed in accordance with the differing requirements of the various embodiments of the present invention. Thus, the abovementioned parameters should not be construed as limiting the scope of the present invention in any way. In addition, it is to be appreciated that the different apertures, rings, sheaths, and other members, described hereinabove may be constructed in different shapes (e.g. having oval, square etc. form in plan view) and sizes differing from those exemplified in the preceding description.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention. For example, one or more of the features described with reference to one embodiment may be added, or omitted, in the other embodiments (e.g., adding an elliptic recess to the about the central aperture of a fixating ring, adding tabs to the removable adapters for preventing rotation thereof or for improving hand grip of the ring etc.). Additionally, the securing, fixating, and interfacing devices and adapters of the invention may be configured in forms different from those exemplified hereinabove in order to allow using them with differently shaped introducers having different geometrical shapes and a similar principal of operation.

The invention claimed is:

1. A securing device for preventing the splitting of a splittable sheath in the body of a treated subject, for facilitating the insertion of a splittable introducer and the splitting of said splittable sheath during removal of said introducer from the body of the subject, and optionally for interfacing said splittable introducer with other devices comprising a "U"-like shaped portion having a distal arm and one or two proximal arms connected by a base, wherein said distal arm comprises an aperture accessible via a vertical slit passing from its upper side and terminating in said aperture, and wherein the gap defined between said distal arm and proximal arms is suitable for fitting a splittable introducer therebetween such that its splittable sheath is retained in the aperture provided in the distal arm and being fully enclosed by said aperture; wherein the width of said slit is less than the diameter of said aperture; and wherein the proximal arm further comprises clasps for retaining the tearing tabs of the splitable introducer fitted thereinto.

2. The device according to claim 1, comprising a single proximal arm, wherein said single proximal arm comprises an aperture accessible via a vertical slit passing from its upper side and terminating in said aperture, wherein the proximal opening of a splittable adapter fitted into said device may be accessed via said aperture provided in said single proximal arm.

3. The device according to claim 2, wherein the aperture provided in the proximal arm provides a tapering passage leading into an opening of the splittable sheath.

4. The device according to claim 2, further comprising locking means attached to the proximal arm, wherein said locking mechanism comprises locking arm attached to an upper side corner of said proximal arm by means of hinge.

5. The device according to claim 4, wherein the base comprise a twisting channel passing along the length of the bottom side thereof and allowing bending said base.

6. The device according to claim 2, wherein the proximal arm connects to the base by means of a hinge such that it is made movable about said hinge.

7. The device according to claim 1, wherein the proximal face of the proximal arm comprises connection means suitable for connecting auxiliary appliances thereto, and for providing a passage therethrough to the apertures provided in the proximal arm.

8. The device according to claim 7, wherein the connection means comprises a longitudinal slit communicating, and preferably aligned, with the slit provided in the proximal arm.

9. The device according to claim 7, wherein the connector means is a type of quick connector.

10. The device according to claim 7, wherein the connector means is of the Luer lock type.

11. The device according to claim 7, wherein the connection means comprises blades attached, or formed, on the inner rim of its longitudinal slit.

12. The device according to claim 1, further comprising an attachment surface attached to the proximal face of the proximal arm(s).

13. The device according to claim 1, wherein the base of the device comprises an angled portion the distal end of which is connected to the distal arm which is elevated relative to the base portion connected to the proximal arm.

14. The device according to claim 1, wherein the proximal face of the distal arm further comprises a recess adapted to retain the distal tips of shanks of the splittable introducer fitted into said device.

15. The device according to claim 1, wherein the base of the device is adapted to prevent rotations thereof about the catheter tube passing therethrough during its insertion.

16. The device according to claim 1, wherein the base of the device comprises a self-adhering strip attached thereto.

17. The device according to claim 1, wherein the vertical slit passes from the bottom side of the distal arm and terminates in the aperture provided therein, and wherein said vertical slit connects to a slit passing along a longitudinal portion of the base of the securing device, and wherein said slit passing along a longitudinal portion of the base may be accessed via a lateral opening provided in said base.

18. The device according to claim 17, wherein the distal arm further comprises fastening means adapted to hold the distal portion of the shanks of a splittable introducer.

19. The device according to claim 1, further comprising enclosing means attached to the distal arm, wherein said enclosing means comprises a base section, attached said distal arm, and a fastening section connected to said base section by means of a hinge.

20. The device according to claim 19, wherein the enclosing means further comprises a locking mechanism.

21. A device for holding the splittable sheath of a splittable introducer and facilitate splitting thereof in a controlled and secure manner, comprising a securing device comprising an aperture adapted to receive and hold the splittable sheath of the splittable introducer, wherein said securing device is designed to be attached to the distal end of the shanks of the splittable introducer; wherein the aperture communicated with a hollow passage and/or a slit passing between said aperture and the edge of the securing device; wherein the securing device comprises a central aperture and a hollow passage and a slit extending radially therefrom, and two releasing tabs provided near said hollow passage, wherein said hollow passage accesses said central aperture of said securing device and terminates near and before the circumference of said securing device at a point between said releasing tabs; wherein the slit comprises a curved portion defining a locking mechanism which may be opened by pressing the releasing tabs towards each other.

22. The device according to claim 21, wherein the slit is located opposite to the hollow passage.

23. The device according to claim 22, wherein the proximal face of the securing device comprises an elliptic recess containing the aperture of said securing device.

24. A device for holding the splittable sheath of a splittable introducer and facilitate splitting thereof in a controlled and secure manner, comprising a securing device comprising an aperture adapted to receive and hold the splittable sheath of the splittable introducer, wherein said securing device is designed to be attached to the distal end of the shanks of the splittable introducer; wherein the aperture communicated with a hollow passage and/or a slit passing between said aperture and the edge of the securing device; wherein the securing device comprises a securing arm and a substantially perpendicular attachment surface attached thereto, wherein said securing arm comprises an aperture adapted to receive and hold the splittable sheath of a splittable introducer, and wherein said aperture may be accessed by an opening provided between the upper side of said securing arm and an upper part of said aperture, and wherein said opening is configured to allow passage of a catheter device therethrough; wherein the proximal face of the securing arm comprises a fastening recess adapted to retain the distal ends of the shanks of the splittable introducer.

25. The device according to claim 24, wherein the inner face of the fastening recess comprises grooves configured to receive respective flanges formed near the distal ends of the shanks.

26. The device according to claim 24, wherein the attachment surface of the device comprises a self-adhering strip attached thereto.

27. A device for holding the splittable sheath of a splittable introducer and facilitate splitting thereof in a controlled and secure manner, comprising a securing device comprising an aperture adapted to receive and hold the splittable sheath of the splittable introducer, wherein said securing device is designed to be attached to the distal end of the shanks of the splittable introducer; wherein the aperture communicated with a hollow passage and/or a slit passing between said aperture and the edge of the securing device, said device comprising two holding arms connected by a base, wherein said arms are configured to hold the distal end of the shanks of the splittable introducer and secure a portion of the splittable sheath near the tips of said shanks; wherein said two holding arms are curved and adjacent, facing each other and comprise an opening between said arms, wherein said opening is adapted for removing a catheter device passing therethrough; and wherein the inner side of said base comprises a detent mechanism tapering portion formed on the inner side of said base adapted for fit in a groove between the shanks of the splittable introducer.

28. The device according to claim 27, further comprising an opening between the arms, wherein said opening is adapted for removing a catheter device passing therethrough.

29. The device according to claim 27, wherein the inner side of the base comprises a detent mechanism adapted for fit in a groove between the shanks of the splittable introducer.

30. A device for holding the splittable sheath of a splittable introducer and facilitate splitting thereof in a controlled and secure manner, comprising a securing device comprising an aperture adapted to receive and hold the splittable sheath of the splittable introducer, wherein said securing device is designed to be attached to the distal end of the shanks of the splittable introducer; wherein the aperture communicated with a hollow passage and/or a slit passing between said aperture and the edge of the securing device; said device comprising two holding arms connected by a base, wherein said arms are configured to hold the distal end of the shanks of the splittable introducer and secure a portion of the splittable sheath near the tips of said shanks; wherein said two holding arms are curved and adjacent, facing each other and comprise an opening between said arms, wherein said opening is adapted for removing a catheter device passing therethrough; and wherein each of the holding arms comprises an inner groove along its length adapted to receive a respective flange formed in, or attached to, the outer surface of a distal end portion of the shanks.

31. A device for holding the splittable sheath of a splittable introducer and facilitate splitting thereof in a controlled and secured manner, comprising a securing device comprising a central aperture adapted to receive and hold the splittable sheath of the splittable introducer, a hollow passage and a slit extending radially therefrom, and two releasing tabs provided near said slit, wherein said hollow passage accesses said central aperture of said securing device and terminates near and before the circumference of said securing device; wherein said slit end is between said releasing tabs; and wherein said slit comprises a curved portion defining a locking mechanism which may be opened by pressing the releasing tabs away from each other.

32. The device according to claim 31, wherein the slit is located opposite to the hollow passage.

33. The device according to claim 31, wherein the slit comprises a curved portion defining a locking mechanism which may be opened by pressing the releasing tabs.

34. The device according to claim 31, wherein the proximal face of said device comprises an elliptic recess containing the aperture of said securing device.

* * * * *